US011185468B2

(12) United States Patent
Coleman et al.

(10) Patent No.: US 11,185,468 B2
(45) Date of Patent: Nov. 30, 2021

(54) UNOBTRUSIVE WIRELESS ELECTRONIC SYSTEMS FOR MONITORING AND FACILITATING PATIENT COMPLIANCE

(71) Applicant: The Regents Of The University Of California, Oakland, CA (US)

(72) Inventors: Todd Prentice Coleman, La Jolla, CA (US); Robert N. Weinreb, Rancho Santa Fe, CA (US); Yun Soung Kim, San Diego, CA (US); Michael Bajema, San Diego, CA (US); Dae Kang, Los Angeles, CA (US); Amr Haj Omar, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1153 days.

(21) Appl. No.: 15/307,283

(22) PCT Filed: Apr. 28, 2015

(86) PCT No.: PCT/US2015/028075
§ 371 (c)(1),
(2) Date: Oct. 27, 2016

(87) PCT Pub. No.: WO2015/168171
PCT Pub. Date: Nov. 5, 2015

(65) Prior Publication Data
US 2017/0046501 A1 Feb. 16, 2017

Related U.S. Application Data

(60) Provisional application No. 61/985,384, filed on Apr. 28, 2014.

(51) Int. Cl.
*A61J 7/04* (2006.01)
*A61J 1/03* (2006.01)
(Continued)

(52) U.S. Cl.
CPC .............. *A61J 1/035* (2013.01); *A61J 7/0418* (2015.05); *A61J 7/0427* (2015.05); *A61J 7/0481* (2013.01);
(Continued)

(58) Field of Classification Search
CPC .............. G06F 19/3456; G06F 19/3462; A61J 7/0427; A61J 7/0418; A61J 1/035; A61J 1/00; A61J 2200/30
See application file for complete search history.

(56) References Cited

U.S. PATENT DOCUMENTS 4,616,316 A * 10/1986 Hanpeter ............... A61J 7/0481
206/531
5,012,496 A 4/1991 Weinreb et al.
(Continued)

FOREIGN PATENT DOCUMENTS

CN   1969743 A    5/2007
EP   0972507 A1   1/2000
(Continued)

OTHER PUBLICATIONS

Wikipedia, "Comparator", retrieved from the Internet URL:https://en.wikipedia.org/w/index.php?title+Comparator&oldid=604831965, Sep. 21, 2017.
(Continued)

*Primary Examiner* — Regis J Betsch
*Assistant Examiner* — Jeremy A Delozier
(74) *Attorney, Agent, or Firm* — Perkins Coie LLP

(57) ABSTRACT

Methods, systems, and devices are disclosed for monitoring the dispensing of a fluid from a container. In one aspect, a system includes a conformal substrate including a mechanically flexible and an electrically insulative material, the substrate attached and conformed to a container containing a fluid; a data acquisition unit including a sensor and a signal
(Continued)

processing circuit formed on the conformal substrate, in which the sensor transduces an occurrence of the fluid dispensing from the container into an electrical signal, and the signal processing circuit amplifies the electrical signal; a data processing unit formed on the conformal substrate and in communication with the data acquisition unit to process the amplified electrical signal as data; and a communications unit formed on the conformal substrate and in communication with the data processing unit to wirelessly transmit the processed data to a remote device.

22 Claims, 17 Drawing Sheets

(51) Int. Cl.
*G16H 20/10* (2018.01)
*G16H 20/13* (2018.01)
*A61F 9/00* (2006.01)

(52) U.S. Cl.
CPC .............. *G16H 20/10* (2018.01); *G16H 20/13* (2018.01); *A61F 9/0008* (2013.01); *A61J 2200/30* (2013.01)

(56) References Cited

U.S. PATENT DOCUMENTS

| | | | |
|---|---|---|---|
| 5,152,424 A | 10/1992 | Weinreb et al. | |
| 5,412,372 A | 5/1995 | Parkhurst et al. | |
| 8,149,096 B2 | 4/2012 | Metry et al. | |
| 8,311,853 B1 | 11/2012 | Pankow et al. | |
| 8,525,677 B2 | 9/2013 | Scharfeld et al. | |
| 8,754,769 B2 | 6/2014 | Stein et al. | |
| 9,311,452 B2 | 4/2016 | Dickie et al. | |
| 9,581,586 B2 | 2/2017 | Shin et al. | |
| 9,600,636 B2 | 3/2017 | Xu et al. | |
| 9,775,780 B2 | 10/2017 | Afsarifard et al. | |
| 10,319,473 B2 | 6/2019 | Fateh et al. | |
| 10,325,479 B2 | 6/2019 | Fateh et al. | |
| 10,497,225 B1 | 12/2019 | Strong et al. | |
| 10,535,248 B2 | 1/2020 | Fateh | |
| 10,617,605 B2 | 4/2020 | Fateh et al. | |
| 10,723,529 B2 | 7/2020 | Strong et al. | |
| 10,811,128 B2 | 10/2020 | Fateh | |
| 2002/0067270 A1 | 6/2002 | Yarin et al. | |
| 2005/0162979 A1 | 7/2005 | Ostergaard et al. | |
| 2006/0231109 A1 | 10/2006 | Howell et al. | |
| 2008/0114490 A1 | 5/2008 | Jean-Pierre | |
| 2010/0314282 A1* | 12/2010 | Bowers | A61J 1/03 206/534 |
| 2011/0050431 A1 | 3/2011 | Hood et al. | |
| 2014/0228783 A1 | 8/2014 | Kraft | |
| 2014/0240094 A1 | 8/2014 | Stein et al. | |
| 2014/0347175 A1 | 11/2014 | Stein et al. | |
| 2015/0019136 A1* | 1/2015 | Medeiros | G01N 33/6893 702/19 |
| 2016/0355322 A1* | 12/2016 | Burton, Jr. | A61J 7/0084 |
| 2019/0103179 A1 | 4/2019 | Fateh et al. | |
| 2019/0252056 A1 | 8/2019 | Fateh | |
| 2019/0295708 A1 | 9/2019 | Fateh | |
| 2020/0095055 A1 | 3/2020 | Cailloux et al. | |
| 2020/0113733 A1 | 4/2020 | Fateh | |
| 2020/0121500 A1 | 4/2020 | Fateh et al. | |

FOREIGN PATENT DOCUMENTS

| | | | |
|---|---|---|---|
| EP | 2269561 A1 | 5/2011 | |
| JP | H080501013 A | 2/1996 | |
| JP | 2006528520 A | 12/2006 | |
| WO | 9407184 A1 | 3/1994 | |
| WO | 199407184 A1 | 3/1994 | |
| WO | 2007077224 A2 | 7/2007 | |
| WO | WO2007/077224 | * | 7/2007 |
| WO | 2011006857 A1 | 1/2011 | |
| WO | 2011127331 A2 | 10/2011 | |
| WO | 2013127564 A1 | 9/2013 | |
| WO | WO2013127564 | * | 9/2013 |
| WO | 2014081570 A1 | 5/2014 | |

OTHER PUBLICATIONS

International Search Report and Written Opinion of International Application No. PCT/US2015/028075; dated Jul. 28, 2015.
Extended European Search Report for European Patent Application No. 15785983.6; dated Oct. 2, 2017, 17 pages.
M M Hermann et al. "Microprocessor controlled compliance monitor for eye drop medication," The British Journal of Ophthalmology, Mar. 2006, pp. 830-832.
U.S. Appl. No. 61/918,554 entitled "Highly scalable fabrication techniques for flexible electronic circuits", filed on Dec. 19, 2013.
Travatan Dosing Aid may improve patient compliance, downloaded Oct. 26, 2016, 2 pages. http://www.eyeworld.org/ewsupplementarticle.phP?id=171.
U.S. Appl. No. 61/994,784 entitled "Fabrication of flexible electronic devices", filed on May 16, 2014.
Office Action for Chinese Patent Application No. 201580031436, dated Jan. 14, 2019, 5 pages.
Office Action for European Patent Application No. 15785983.6, dated Apr. 10, 2019, 6 pages.
Decision of Refusal for Japanese Patent Application No. 2016-565025, dated Aug. 6, 2019, 3 pages.
Office Action for Japanese Patent Application No. 2016-565025, dated Feb. 21, 2019, 5 pages.
Office Action for Chinese Patent Application No. 201580031436, dated Aug. 26, 2019, 9 pages.
JPO, Trial and Appeal Decision for Japanese Patent Application No. 2016-163602. dated Jan. 12, 2021. Original & English translation. 24 pages.
CNIPA, Third Office Action for Chinese Patent Application No. 201580031436.X. dated Mar. 6, 2020. 7 pages. Machine translation in English obtained from USPTO Global Dossier.
IPA, Examination Report No. 1 for Australian Patent Application No. 2015253309. dated Feb. 28, 2020. 4 pages.
CNIPA, Fourth Office Action for Chinese Patent Application No. 201580031436.X. dated Oct. 12, 2020. 8 pages. Machine translation in English obtained from USPTO Global Dossier.

* cited by examiner

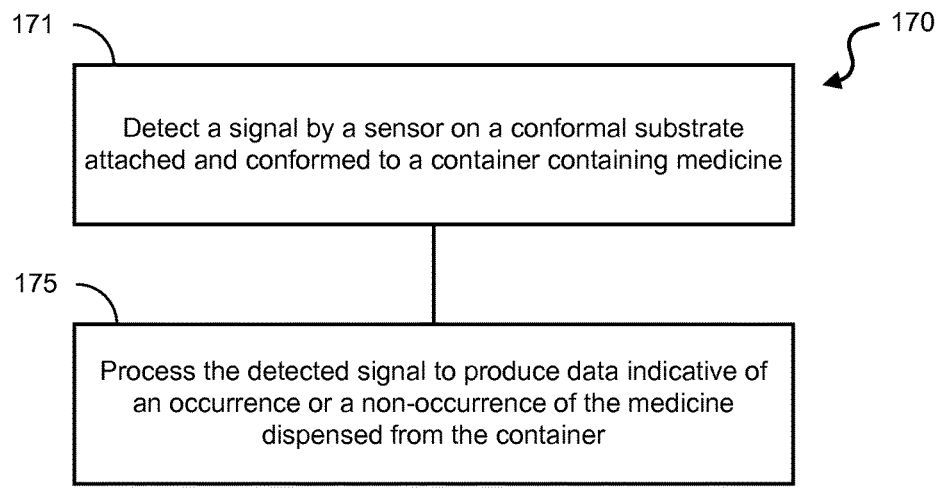
FIG. 1D
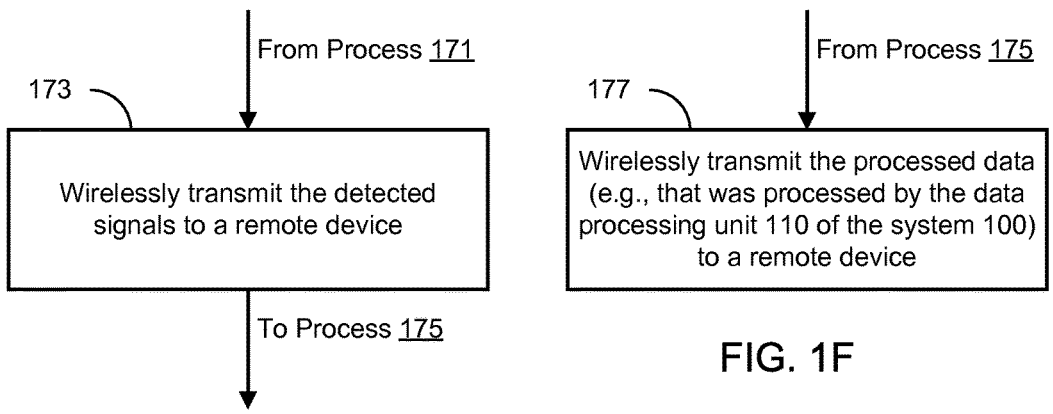
FIG. 1E
FIG. 1F
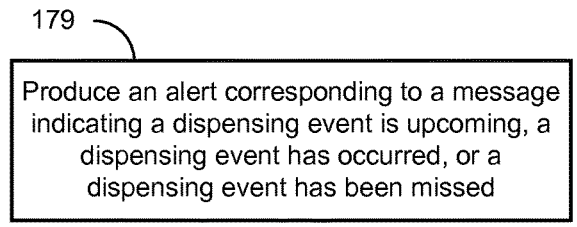
FIG. 1G

UNOBTRUSIVE WIRELESS ELECTRONIC SYSTEMS FOR MONITORING AND FACILITATING PATIENT COMPLIANCE

CROSS REFERENCE TO RELATED APPLICATIONS

This patent document is a 35 USC § 371 National Stage application of International Application No. PCT/US2015/028075, entitled "UNOBTRUSIVE WIRELESS ELECTRONIC SYSTEMS FOR MONITORING AND FACILITATING PATIENT COMPLIANCE," filed on Apr. 28, 2015, which claims the benefits and priority of U.S. Provisional Patent Application No. 61/985,384, entitled "UNOBTRUSIVE WIRELESS ELECTRONIC SYSTEMS FOR MONITORING AND FACILITATING PATIENT COMPLIANCE", filed on Apr. 28, 2014. The entire contents of the aforementioned patent applications are incorporated by reference as part of the disclosure of this application.

TECHNICAL FIELD

This patent document relates to systems, devices, and processes that use thin flexible electronic sensor technologies.

BACKGROUND

Flexible electronics can include electric circuits and devices formed on flexible substrates that can be applied to and conform to a variety of surface geometries. For example, flexible electronics have a key advantage that they can wrap arbitrary, curvilinear surfaces and, at the same time, achieve mechanical properties that approach those of the carrier substrate that the flexible electronics are mounted or integrated.

SUMMARY

Techniques, systems, and devices are disclosed for implementing unobtrusive wireless electronics on containers of medical substances (e.g., prescription drugs) for monitoring and facilitating patient compliance. In some implementations, for example, flexible electronic sensor and wireless communication systems are employed on pharmaceutical bottles or containers, e.g., including patient alert features, for assisting patient compliance of medication schedules.

In one aspect, a device for monitoring patient compliance of a medication includes a substrate that is attachable and conformable to a container containing medicine; a data acquisition unit including a sensor and a signal processing circuit formed on the substrate, in which the sensor is operable to transduce an occurrence of the medicine dispensing from the container into an electrical signal, and the signal processing circuit is operable to amplify the electrical signal; a data processing unit including a processor and a memory formed on the substrate and in communication with the data acquisition unit to process the amplified electrical signal as data; and a communications unit formed on the substrate and in communication with the data processing unit to wirelessly transmit the processed data to a remote device.

In one aspect, a method for monitoring dispensing of medicine from a container includes detecting a signal by a sensor on a conformal substrate attached and conformed to a container containing medicine; and processing the detected signal to produce data indicative of an occurrence or a non-occurrence of the medicine dispensed from the container.

In one aspect, a device for monitoring dispensing of a fluid from a container includes a data acquisition unit including a sensor and a signal processing circuit formed in a material structure of a container capable of storing and dispensing a fluid, in which the sensor transduces an occurrence of the fluid dispensing from the container into an electrical signal, and the signal processing circuit amplifies the electrical signal; a data processing unit including a processor and a memory unit, the data processing unit formed in the material structure of the container and in communication with the data acquisition unit to process the amplified electrical signal as data to determine a dispensing event of the fluid from the container; and a communications unit formed in the material structure of the container and in communication with the data processing unit to wirelessly transmit the processed data to a remote device.

In one aspect, a device for monitoring dispensing from a container includes a substrate that is attachable and conformable to a container; a data acquisition unit including a sensor and a signal processing circuit formed on the substrate, in which the sensor is operable to transduce an occurrence of a content contained in the container dispensing from the container into an electrical signal, and the signal processing circuit is operable to amplify the electrical signal; and a communications unit formed on the substrate and in communication with the signal processing circuit to wirelessly transmit the amplified electrical signal to a remote device.

Those and other features are described in greater detail in the drawings, the description and the claims.

BRIEF DESCRIPTION OF THE DRAWINGS

FIGS. 1D-1G show block diagrams of an exemplary method to monitor dispensing of medicine from a container.

DETAILED DESCRIPTION

Figure 1A:
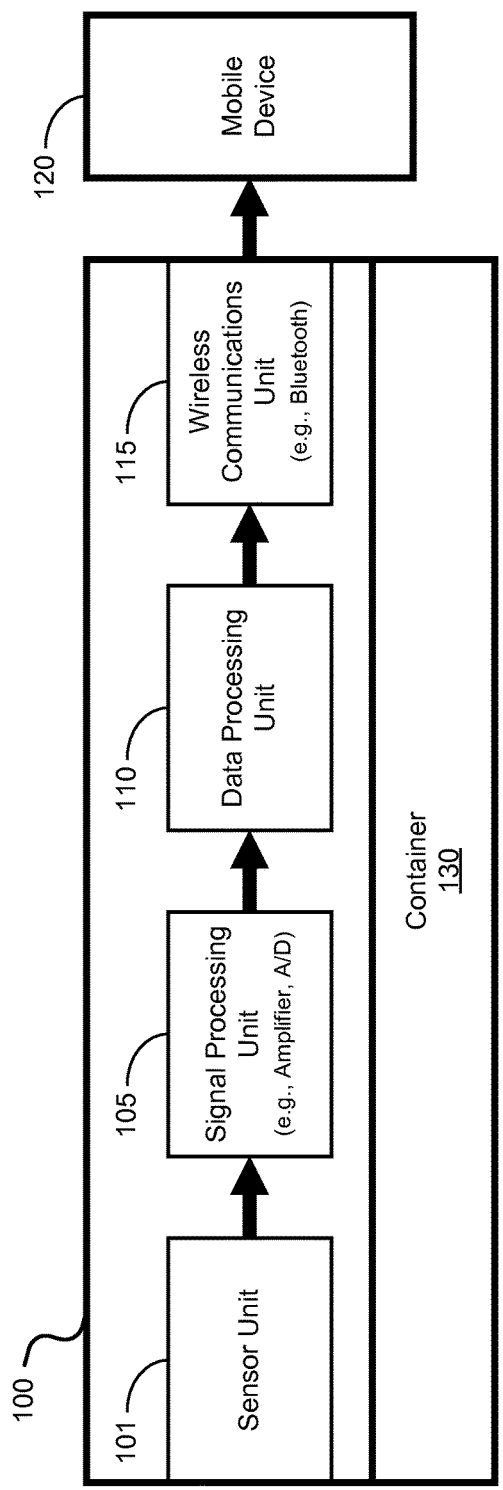
FIG. 1A shows a block diagram of an exemplary flexible electronics system of the disclosed technology to monitor dispensing of a fluid from a container by a user.

Patient compliance for use of medications or other controlled substances is an important part of a medical treatment or healthcare of a patient. Currently, the ability to monitor patient compliance is limited by several factors. For example, most bottles or containers of medications lack a built-in monitoring system, and thus physicians and other caregivers cannot determine how the patient is doing. Also, the relatively few bottles or containers that include some monitoring mechanisms tend to have rigid, thick, and/or heavy components (e.g., such as electronics) that render the bottle/container in an obtrusive form factor and thus compromise the convenience for the patient in normal situations. If the ergonomics of the bottle are too unobtrusive or too heavy (e.g., where the bottle cannot fit in the user's pocket, purse or other carrier or not even convenient to carry in hand), then such compliance systems may not receive acceptance by patients and thus defeat the point of their own use—or worse, such obtrusive or cumbersome compliance monitoring systems may cause non-compliance. There is a significant unmet need for accurate patient compliance in a manner that has the same form factor or a very close form factor to the bottle/container/pack of medicine that otherwise does not include compliance monitoring technologies. Moreover, in the case of drop dispensing bottles, millions of dollars have already been spent on use-cases and studies to determine the optimal bottle size, shape, etc. for not only delivering accurate drops, but for maximizing patient utility. Therefore, it is important that patient compliance monitoring systems are unobtrusively integrable into such optimized container designs.

The disclosed technology describes multiple approaches and system designs using ultra-thin flexible electronics to inconspicuously monitor patient compliance, and provide avenues to intervene and encourage such compliance. The disclosed ultra-thin flexible electronics techniques, systems, and devices can be employed in existing designs of medicine bottles, blister packs and other type containers, which obviate the need to study, develop and optimize new types of bottles (i.e., start from the drawing board in terms of patient utility).

In some examples, the disclosed technology uses flexible electronics and wireless communications telemetry to monitor when a drop is dispensed from a bottle or a pill is dislodged from a blister pack, stores the data associated with the patient's monitored action in memory (e.g., such as a local memory in the flexible electronics), and transmits to a data processing device, e.g., such as a user's mobile communications device (e.g., smartphone, tablet, or wearable computing/communications device like a 'smartwatch', 'smartglasses', etc.). Moreover, in some example embodiments, the disclosed flexible electronics unit unobtrusively employed to the medicine container may include LED indicators or other indicators or transducers and logic inside the flexible electronics circuits to adapt to when events have occurred and provide sensory cues (e.g., visual, auditory, or haptic reminders) to the subject.

Techniques, systems, and devices are disclosed for implementing unobtrusive wireless electronics on containers of medical substances (e.g., including prescription drugs) for monitoring and facilitating patient compliance.

In one aspect, a device for monitoring the dispensing of a medicine from a medicine container includes a data acquisition unit, and a wireless communications unit formed on a conformal substrate that is attached to a container containing medicine such that the device is inconspicuously integrated with the container. In some embodiments, the device includes a data processing unit formed on the conformal substrate and in communication with the data acquisition and the wireless communication unit. In some implementations, the substrate includes a mechanically flexible (e.g., stretchable and bendable) and an electrically insulative material. The data acquisition unit includes a sensor and a signal processing circuit, in which the sensor is operable to transduce an occurrence of the medicine dispensing from the container into an electrical signal, and the signal processing circuit is operable to amplify the electrical signal. The communications unit is in communication with the signal processing circuit and/or the data processing unit to wirelessly transmit the amplified signal or the processed data to a remote device. The data processing unit is in communication with the data acquisition unit and includes a processor and a memory to process the amplified electrical signal as data.

In some implementations of the disclosed flexible electronic sensor and wireless communication technology, the device can be applied to or integrated into bottles or other type containers of various types of fluids, e.g., including, but not limited to, prescription and nonprescription drugs such as eye drops. The disclosed flexible electronic device can be used to monitor the usage of such fluids by a user of the bottle or container. For example, in some implementations, the flexible electronic device can include user alert communication modules that provide communicative signals from the device to the user, e.g., for assisting patient compliance of medication schedules. For example, the flexible electronic device can be used to infer the release of medication from an eye drop bottle to which the device is applied or integrated. The dispensing time can be recorded by sensors and processed by the device, which can be used to provide the user with real-time feedback to encourage patient compliance. Also, for example, the disclosed flexible electronic sensor device can be utilized to assess adherence and compliance in the evaluation of new drugs during clinical research trials.

Current state of the art sensor systems are obtrusive to a user by making the bottle bulkier. Also, many existing sensor systems are specific to a certain medicine, i.e., interact with the medication. Conversely, the disclosed flexible electronic sensor system is designed to be implemented within any conformation or geometry of existing bottles, e.g., which in some implementations can be wrapped around the bottle with minimal obtrusion using thin, flexible electronics. For example, the flexible electronic units of the disclosed technology can be incorporated with existing medicine container droplet bottles, blister packs, or other container forms such that flexible electronic units retain the look, feel, and operation of the medicine container. Implementation of the disclosed technology does not change or create complications in the medicine container design, medicine container fabrication process, or the medicine's regulatory process. For example, the disclosed flexible electronics units can be implemented on medicine containers such that the flexible electronics units do not interact with the medication.

In one example, an exemplary flexible electronics patient compliance device can be integrated with a labeling wrapped around a droplet bottle for a particular medicine (e.g., eye drops), or attached and conformed on the droplet bottle after the medicine is enclosed prior to or concurrently with application of the labeling, where the labeling can be attached over or away from the exemplary flexible electronics patient compliance device. The exemplary device can be applied to the exterior of the medicine container after the medicine has been enclosed or sealed within the container.

Exemplary Embodiments

FIG. 1A shows a diagram of an exemplary flexible electronics system 100 to monitor dispensing of a fluid from a container 130 by a user (e.g., a patient). The system 100 includes a sensor unit 101 to transduce an occurrence of use of the container 130 into an electrical signal, e.g., including the dispensing of an amount of fluid and/or change in orientation of the container 130. The system 100 includes a signal processing unit 105 to process the captured electrical signals of the sensor unit 101, e.g., such as amplification and other signal conditioning, and/or conversion from an analog signal to a digital signal. The system 100 includes a data processing unit 110 including a processor and a memory to process and store or buffer the processed signals as data. The system 100 includes a wireless communication unit 115 to transmit the processed data to another remote device, e.g., such as a mobile communications device 120, as shown in FIG. 1A. For example, the wireless communications unit 115 can be configured to transmit and receive data from the remote device. FIG. 1C shows an illustrative diagram of the exemplary flexible electronics system 100 inconspicuously attached to the container 130 and in wireless communication with the mobile communications device 120.

The system 100 can be configured in wireless communications with the mobile communications device 120 of the user, e.g., to provide an alert to the user to utilize the fluid in the container 130, e.g., such as a medication. For example, the system 100 can be used to record information about the timing and/or quantity of fluid dispensed (e.g., such a drop), in which this information is logged with circuitry attached on the container 130 and used to provide the user for feedback on his/her use, e.g., via the mobile communications device 120.

In some implementations, for example, the flexible electronics system 100 can be configured in a device package including a substrate that includes a mechanically flexible material (e.g., bendable and/or stretchable) structured to mechanically conform to and/or adhere to the exterior of the container 130 to substantially match the form factor of the container 130, or to mechanically conform to and/or integrate within the material of the container 130. For example, the substrate can include, but is not limited to, polydimethylsiloxane (PDMS), consumer grade adhesives (e.g., 3M Scotch® Tape and Tegaderm™), and other thin film materials including silicon-based, polyimide-based thin films. The substrate can be configured to have a thickness in a range of a few millimeters to tens of microns, e.g., such as 10 µm thickness. For example, the device package of the system 100 can be configured to have a thickness approximate to that of a piece of paper (e.g., 50 µm). The system 100 can be attached to the container 130 in a variety of exemplary embodiments. For example, any of the units of the system 100, e.g., including the sensor unit 101, the signal processing unit 105, the data processing unit 110, and/or the wireless communications unit 115, can be implemented in a single device package attached to the container 130 or in various combinations of device packages that are attached to the container 130 and in communication with the other(s).

In some implementations, for example, the signal processing unit 105 can include transistors, capacitors, resistors, inductors, transistors, diodes, amplifiers, and/or other circuit elements, etc., to process the captured signals acquired by the sensor unit 101. Some examples of the signal processing unit 105 are described later.

Figure 1B:
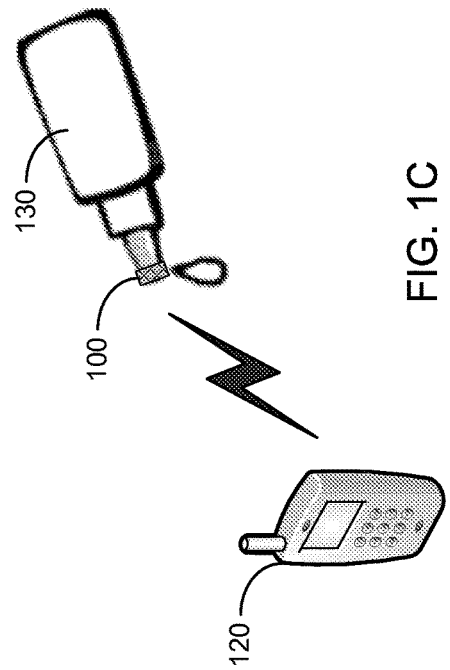
FIG. 1B shows a block diagram of an exemplary data processing unit of the exemplary flexible electronics system.
Figure 1C:
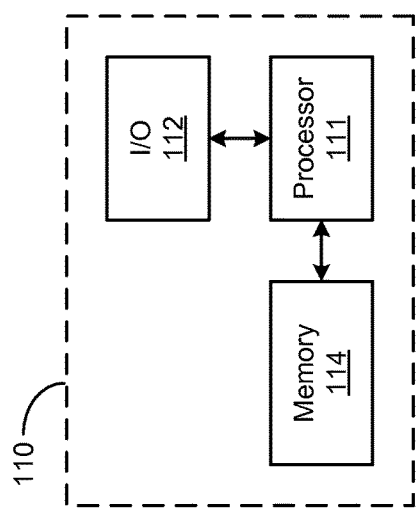
FIG. 1C shows an illustrative diagram of the exemplary flexible electronics system shown in FIG. 1A.

FIG. 1B shows a block diagram of an exemplary data processing unit of the exemplary flexible electronics system. As shown in FIG. 1B, the data processing unit 110 can include a processor 111 to process data and a memory 114 in communication with the processor 111 to store data. For example, the processor 111 can include a central processing unit (CPU) or a microcontroller unit (MCU). For example, the memory 114 can include processor-executable code, which when executed by the processor 111, configures the data processing unit 110 to perform various operations, such as receiving information, commands, and/or data, processing information and data, and transmitting or providing information/data to another entity or to a user. For example, the data processing unit can include a power supply to provide power to components of the system 100, e.g., such as unobtrusive batteries, autonomously generated power supply units (e.g., such as photovoltaic cells) or wireless powering units.

To support various functions of the data processing unit 110, the memory 114 can store other information and data, such as instructions, software, values, images, and other data processed or referenced by the processor 111. Various types of Random Access Memory (RAM) devices, Read Only Memory (ROM) devices, Flash Memory devices, and other suitable storage media can be used to implement storage functions of the memory 114. The memory 114 can store data and information of the data processing unit 110 and other units of the system 100, e.g., including the communications unit 115, the sensor unit 101, and/or the signal processing unit 105, as well as information about other systems and devices in communication with the system 100. For example, the memory 114 can store device unit parameters, and hardware constraints, as well as software parameters and programs of the mobile device 120.

The data processing unit 110 can include an I/O unit 112 that can allow communicative connectability of the data processing unit 110 to other units of the system 100. For example, the data processing unit 110 can be configured in communications with other units of the system 100, e.g., which can be configured in a separate casing or module attached to container 130, using various types of wired or wireless interfaces compatible with typical data communication standards, for example, including, but not limited to, Universal Serial Bus (USB), IEEE 1394 (FireWire), Bluetooth, IEEE 802.111, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, and parallel interfaces. The I/O unit 112 can also provide communicative connectability of the data processing unit 110 to an external interface, source of data storage, or display device. The I/O unit 112 of the data processing unit 110 can also interface with other external interfaces, sources of data storage, and/or visual or audio display devices, etc. to retrieve and transfer data and information that can be processed by the processor 111, stored in the memory 114, or exhibited on an output unit of the mobile communications device 120.

Referring back to FIG. 1A, the mobile communications device 120 can include a smartphone, tablet, or wearable communications device (e.g., such as a smartwatch, smartglasses, etc.). In some implementations, for example, the mobile communications device 120 can also include a communications receiver on a personal computer, e.g., such as a desktop or laptop computer, or on another computer system. For example, data sent to the mobile communications device 120 can be subsequently sent by the device 120 to a computer system or communication network accessible via the Internet (referred to as 'the cloud') that includes one or more remote computational processing devices (e.g., servers in the cloud). For example, various types of wired or wireless interfaces compatible with typical data communication standards can be used in communications of the system 100 with the mobile communications device 120, e.g., including, but not limited to, a cable link such as the Universal Serial Bus (USB) or IEEE 1394 (FireWire), or a wireless link based on an RF communication protocol such as a near-field communication protocol, Bluetooth, IEEE 802.111, or other communication links including, e.g., Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, and parallel interfaces.

The sensor unit 101 can be configured to include one or more of the following exemplary sensors on the flexible, stretchable substrate, e.g., including, but not limited to, 1) temperature sensor; 2) optical sensor; 3) force/pressure sensor; and 4) position sensor. One or multiple sensor units 101 may be unobtrusively attached to the container 130, e.g., such as one or a plurality of a particular type sensor attached to one region of the container 130, and one or a plurality of a different or the same type sensor attached to another region of the container 130. For example, a droplet dispenser container may have an optical sensor of the disclosed technology attached to the nozzle region of the dispenser and may have a pressure sensor of the disclosed technology attached to the body region (e.g., squeezable region) of the container. Also, for example, the droplet dispenser container may have a position sensor of the disclosed technology attached to the body, and/or nozzle region of the dispenser, and/or may have a temperature sensor of the disclosed technology attached to the nozzle region.

FIG. 1D shows a block diagram of a method 170 to monitor dispensing of medicine from a container, e.g., which can include monitoring patient compliance for use of the medicine. The method 170 includes a process 171 to detect a signal by a sensor on a conformal substrate attached and conformed to a container containing medicine. In some implementations of method 170, for example, the process 171 can be implemented by the system 100 unobtrusively attached to or integrated with the container containing medicine, e.g., in which the system 100 can use one or more of sensors and types of sensors on the flexible, stretchable substrate, e.g., the temperature sensor, optical sensor, force/pressure sensor, and position sensor. The method 170 includes a process 175 to process the detected signal to produce data indicative of an occurrence or a non-occurrence of the medicine dispensed from the container.

Implementations of the method 170 can include one or more of the following features. In implementations, for example, the process 171 can include transducing events corresponding to the medicine dispensing and not dispensing from the container into distinguishable electrical signals, and amplifying the electrical signals. In some implementations, for example, the process 175 can include determining an amount of the medicine dispensed from the container based on the detected signal. In some implementations, for example, the process 175 can include associating a time value with a determined occurrence, and can also include determining if the time value associated with the determined occurrence is before or after a predetermined time (e.g., such as based on a medication use schedule, which may be provided by a caregiver or based on the prescription), which can be used to indicate the degree or level of patient compliance.

In some implementations of the method 170, for example, the process 175 can be performed by the data processing unit 110 on the conformal substrate 102 of the system 100; and/or in some implementations of the method 170, for example, the process 175 can be performed by a processing unit on a remote device (e.g., such as the user's mobile device 120, and/or another remote computing device such as a server in the cloud). As shown in FIG. 1E, in some implementations, the method 170 can include a process 173 to wirelessly transmitting the detected signals to the remote device that includes a processing unit to implement the process 175. As shown in FIG. 1F, in some implementations, the method 170 can include a process 177 to wirelessly transmit the processed data that was processed by the data processing unit 110 of the system 100 to the remote device. As shown in FIG. 1G, the method 170 can include a process 179 to produce an alert (e.g., which can be displayed by an alert unit of the system 100 (e.g., LED or other light emitter, audio speaker, or haptic unit such as a vibrator including a motor coupled to a gear), or which can be displayed by the user's mobile device 120) corresponding to a message indicating a dispensing event is upcoming, a dispensing event has occurred, or a dispensing event has been missed.

Temperature Sensing

In some embodiments, the sensor unit 101 can include one or more temperature sensors 101a (e.g., such as a temperature dependent resistive flow sensor). For example, the exemplary temperature dependent resistive flow sensors 101a can be formed using a material with temperature sensitive resistance, e.g., such as platinum. In implementations of the system 100, a temperature fluctuation occurs when liquid passes over the nozzle of the container 130. This translates to a change in resistance on the exemplary temperature dependent resistive flow sensors 101a of the system 100, which can acquire the signal and process the signal into data to indicate that an amount of the liquid (e.g., such as a drop) was released from the container 130.

Figure 2A:
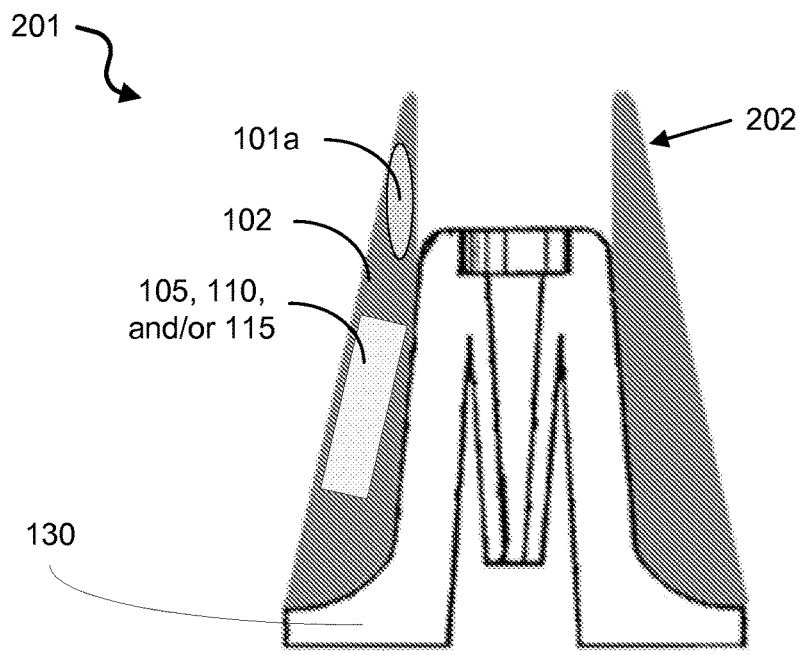
FIGS. 2A and 2B show diagrams of an exemplary temperature data acquisition unit of a flexible electronics system of the disclosed technology unobtrusively attached to a droplet dispenser to monitor droplet dispensing from a container.

FIG. 2A shows a cross-sectional diagram of an exemplary temperature data acquisition unit 201 of the disclosed technology unobtrusively attached to a droplet dispenser to detect the dispensing of a droplet from a container, e.g., in which the detected dispensing data can be processed for monitoring patient compliance. As shown in the diagram of FIG. 2A, the temperature data acquisition unit 201 is attached to or integrated in a conformal substrate 102 of the system 100 that is attachable to the container 130, e.g., shown attached to the nozzle region of the container 130, and such that the system 100 is inconspicuously integrated with the container 130. In the exemplary embodiment shown in FIG. 2A, a region 202 of the conformal substrate 102 can be configured to partially protrude past the opening of the nozzle of the container 130. The temperature data acquisition unit 201 includes a temperature sensor 101a, e.g., such as a temperature-dependent resistive flow sensor, configured on the conformal substrate 102 in the region 202. In some implementations, for example, the temperature sensor 101a can be embedded on an interior side of the substrate 202 of the region 202 such that a dispensed droplet passes through the interior passage of the region 202 to cause a temperature-based change on the temperature sensor 101a, e.g., such as change in resistance on the exemplary temperature-dependent resistive flow sensor. The temperature sensor 101a is in communication with the signal processing circuit 105, e.g., which can amplify and/or modulate the detected signal for data processing by the data acquisition unit 110, and/or for transmission to the device 120 by the wireless communication unit 115.

Figure 2B:
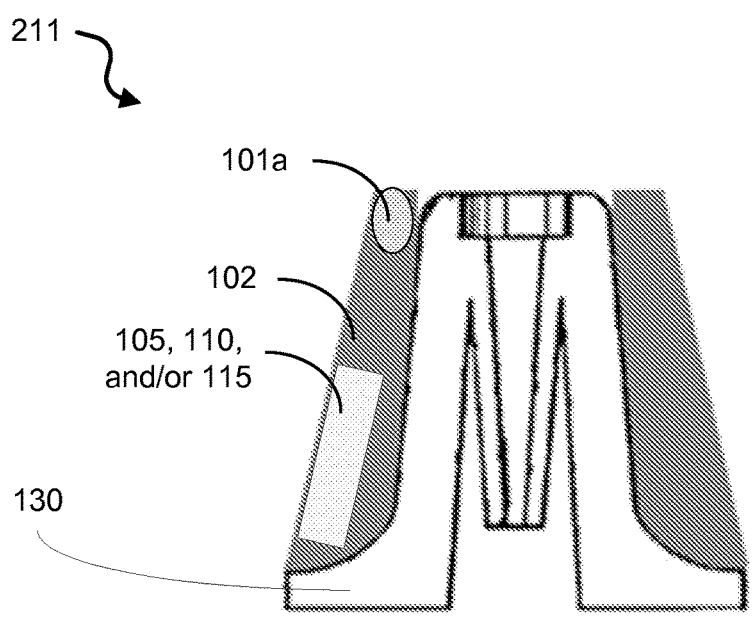

FIG. 2B shows a cross-sectional diagram of another exemplary temperature data acquisition unit 211 of the disclosed technology unobtrusively attached to a droplet dispenser to detect the dispensing of a droplet from a container. As shown in the diagram of FIG. 2B, the temperature data acquisition unit 211 is attached to or integrated in the conformal substrate 102 of the system 100 that is attachable to the nozzle of the container 130, such that the temperature sensor 101a is configured on the conformal substrate 102 proximate the tip of the nozzle to detect a dispensed droplet as it passes out of the opening of the nozzle to cause a temperature-based change on the temperature sensor 101a.

Figure 2C:
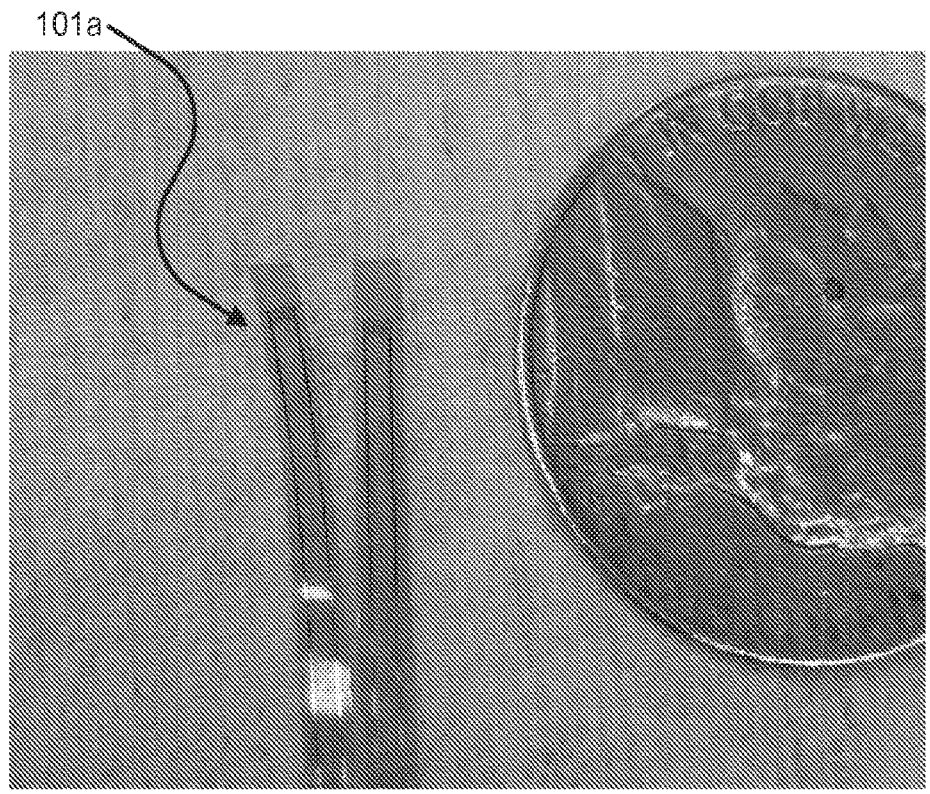
FIGS. 2C-2F show images and diagrams of exemplary flexible temperature sensor systems to monitor dispensing of a droplet from a container nozzle.
Figure 2D:
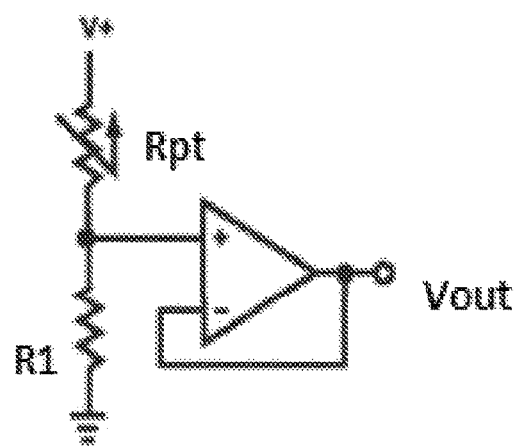
Figure 2E:
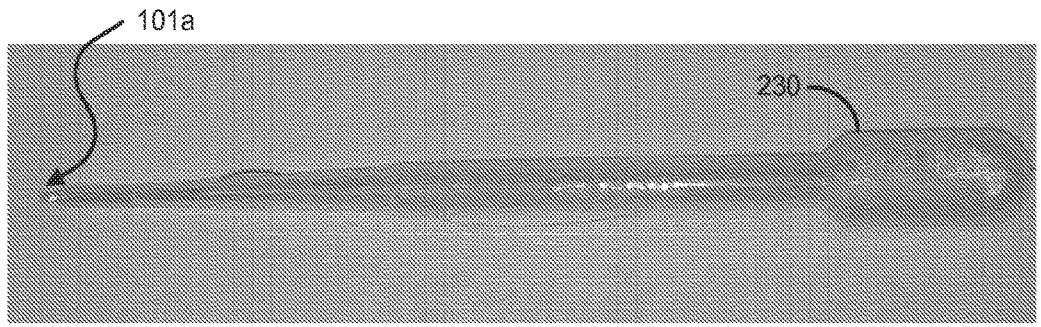
Figure 2F:
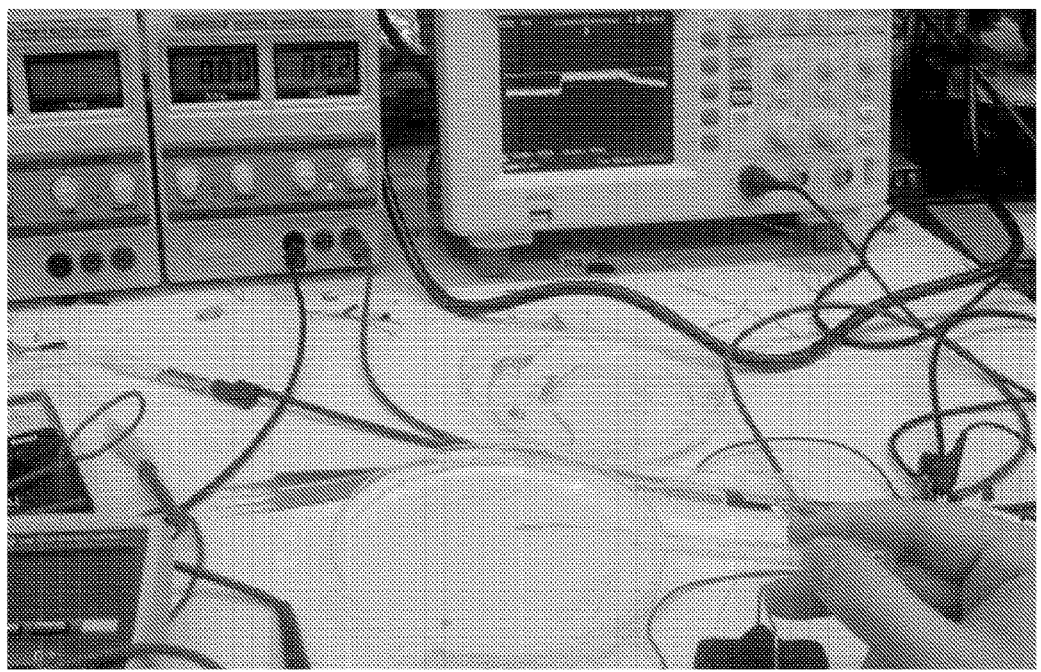

FIGS. 2C-2F show images and diagrams of an exemplary system to monitor dispensing of a droplet using the exemplary flexible sensor unit including a temperature dependent resistive flow sensor attached to a droplet dispenser. The images and diagrams of FIGS. 2C-2F show some aspects of the disclosed technology that may be included in various embodiments of the system 100. FIG. 2C shows an image of an example temperature dependent resistive flow sensor 101a of the flexible sensor unit 101, which is structured to include a platinum resistor electrically coupled to an electronic circuit. FIG. 2D shows a diagram of the electronic circuit and the platinum resistor to produce an output voltage based on a transduced occurrence detected by the sensor 101a, e.g., such as acquiring an eye drop at or near the tip of a container. FIG. 2E shows an image of an exemplary container 230, e.g., such as a droplet pipette, having attached to it an exemplary embodiment of the system 100 including the temperature dependent resistive flow sensor 101a to detect the dispensing of a droplet from the pipette 230. FIG. 2F shows an image depicting the set-up of an exemplary implementation of the system 100 employed on the pipette 230, including the exemplary temperature dependent resistive flow sensor 101a wired to a remote signal processing and data processing unit.

Optical Sensing

In some embodiments, the sensor unit 101 can include one or more optic flow sensors 101b. In such implementations, for example, a light emitting diode (LED) of the optical flow sensor unit 101b can be placed on the nozzle of the container 130 across from a photodetector of the optical flow sensor unit 101b. For example, as fluid passes through the nozzle, the refraction index changes in between the LED and photodetector. This translates to a change in the amount of light on the photodetector that is measured by a voltage change across the photodetector of the optic flow sensor unit 101b and processed to indicate that an amount of the liquid (e.g., such as a drop) was released from the container 130. For example, the measured signal (e.g., voltage change) can be amplified by the signal processing unit 105, and the processed signal subsequently sent to the data processing unit 110 (e.g., such as a microcontroller).

Figure 3A:
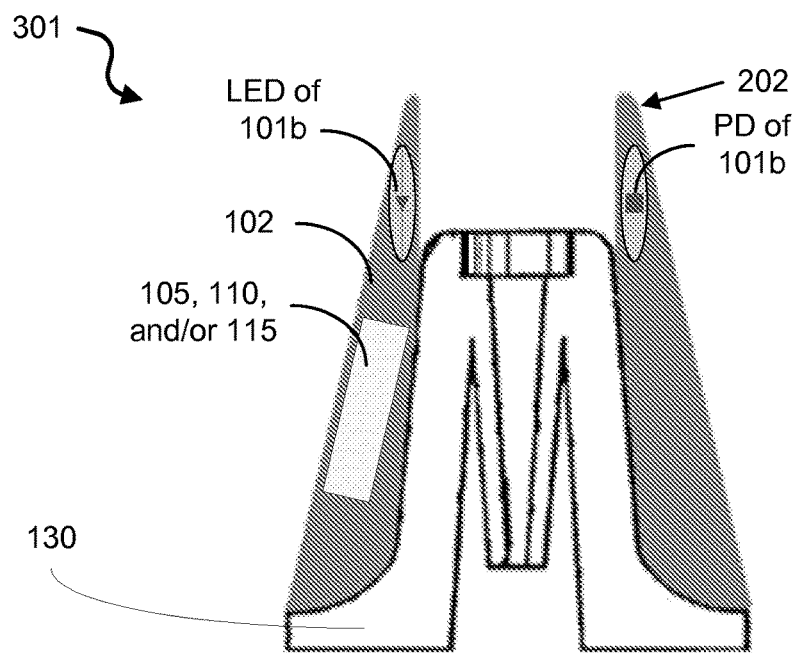
FIGS. 3A and 3B show diagrams of an exemplary optical data acquisition unit of a flexible electronics system of the disclosed technology unobtrusively attached to a droplet dispenser to monitor droplet dispensing from a container.

FIG. 3A shows a cross-sectional diagram of an exemplary optical data acquisition unit 301 of the disclosed technology unobtrusively attached to a droplet dispenser to detect the dispensing of a droplet from a container, e.g., in which the detected dispensing data can be processed for monitoring patient compliance. As shown in the diagram of FIG. 3A, the optical data acquisition unit 301 is attached to or integrated in the conformal substrate 102 of the system 100 that is attachable to the container 130, e.g., shown attached to the nozzle region of the container 130, and such that the system 100 is inconspicuously integrated with the container 130. In the exemplary embodiment shown in FIG. 3A, the optical data acquisition unit 301 includes an optical sensor assembly 101b, e.g., including an LED placed on or embedded in the substrate 102 on an interior side of the substrate 102 within region 202, and a photodetector placed on or embedded in the substrate 102 on the opposite interior side of the substrate 102 within region 202. The optical sensor assembly 101b is configured on the conformal substrate 102 such that a dispensed droplet that passes through the interior passage of the region 202 will cause an optical-based change on the optical sensor assembly 101b, e.g., such as a refraction index change in between the LED and photodetector, where a change in the amount of light on the photodetector is transduced to a voltage change at the photodetector of the optical sensor assembly 101b. The optical sensor assembly 101b is in communication with the signal processing circuit 105, e.g., which can amplify and/or modulate the detected signal for data processing by the data acquisition unit 110, and/or for transmission to the device 120 by the wireless communication unit 115.

Figure 3B:
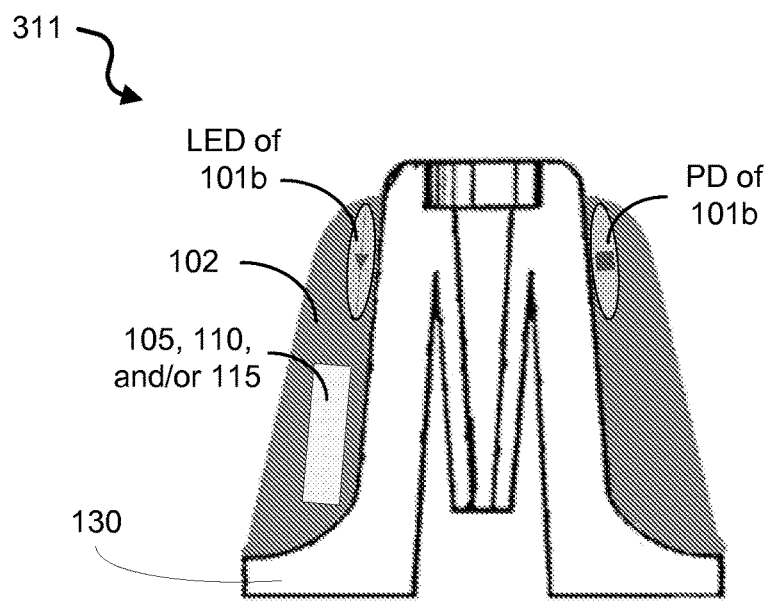

FIG. 3B shows a cross-sectional diagram of another exemplary optical data acquisition unit 311 of the disclosed technology unobtrusively attached to a droplet dispenser to detect the dispensing of a droplet from a container. As shown in the diagram of FIG. 3B, the optical data acquisition unit 311 is attached to or integrated in the conformal substrate 102 of the system 100 that is attachable to the nozzle of the container 130, such that the system 100 is inconspicuously integrated with the container 130. In the exemplary embodiment shown in FIG. 3B, the optical data acquisition unit 311 includes the optical sensor assembly 101b configured on the conformal substrate 102 proximate the tip of the nozzle of the container 130 to detect a dispensed droplet as it passes out of the opening of the nozzle to cause an optical-based change on the optical sensor assembly 101b.

Figure 3C:
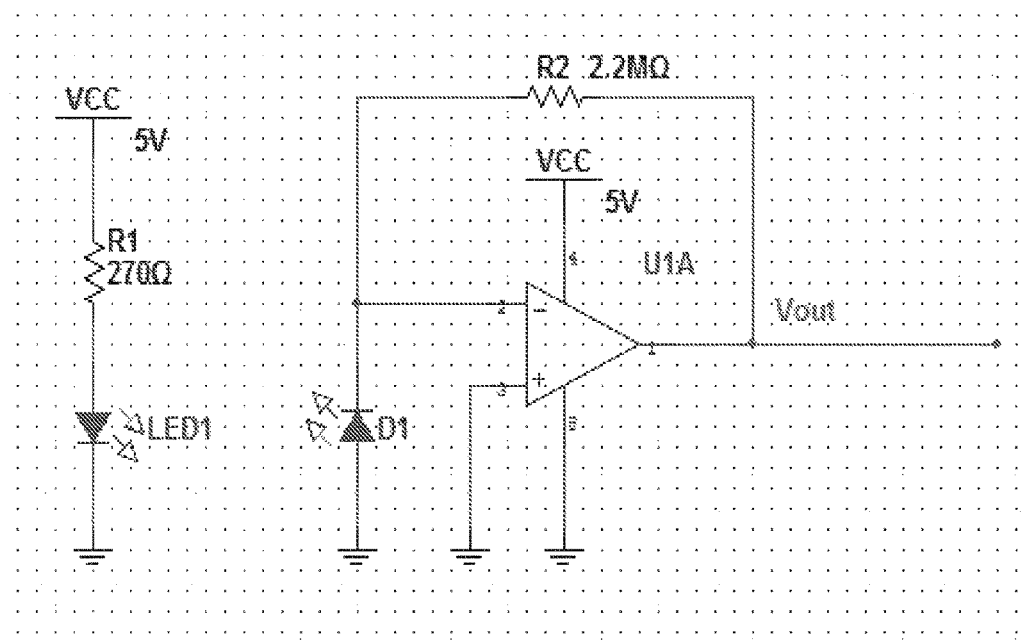
FIGS. 3C-3D show diagrams and images of exemplary flexible optical sensor systems to monitor dispensing of a droplet from a container nozzle.
Figure 3D:
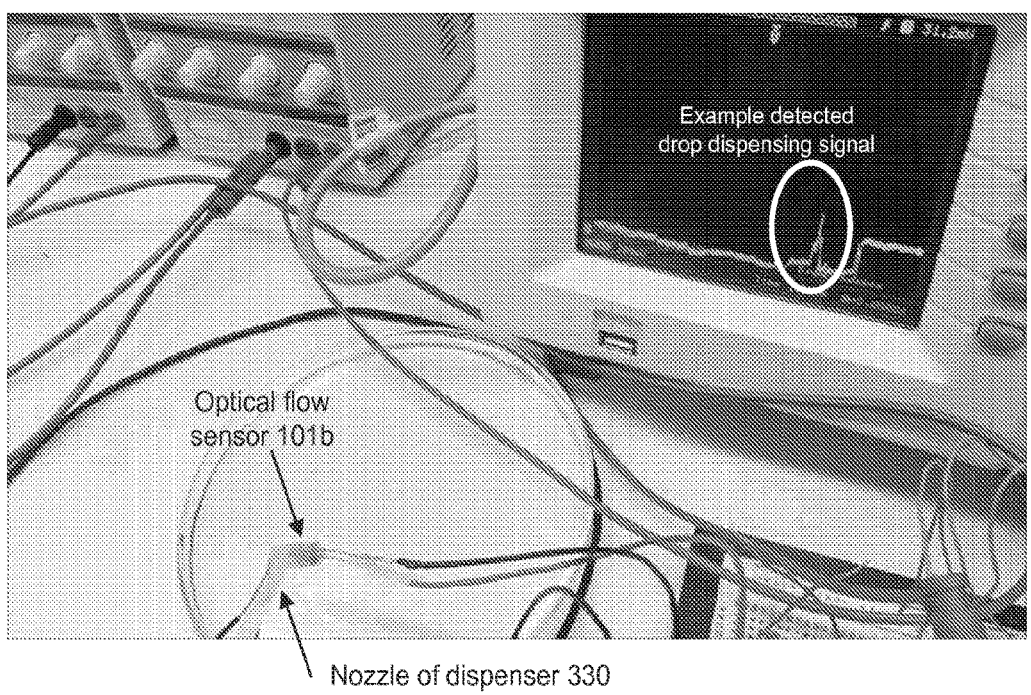

FIGS. 3C-3D show diagrams and images of exemplary flexible optical sensor systems to monitor dispensing of a droplet from a container nozzle. FIG. 3C shows a diagram of an exemplary circuit diagram to implement an exemplary amplification scheme to process the detected signal by the optical flow sensor. For example, as shown in the circuit diagram of FIG. 3C, the element labeled D1 represents the photodetector of the optical flow sensor and the element labeled LED1 represents the LED of the optical flow sensor. FIG. 3D shows an image depicting an exemplary set-up for implementation of the system 100 conformed on a droplet dispenser and including an optical data acquisition unit to optically detect the dispensing of a droplet form the dispenser. For example, as shown in FIG. 3D, flexible optoelectronics including an exemplary optical flow sensor 101b are attached at the base of a drop dispenser 330, e.g., on the outside of a nozzle, and an oscilloscope in the background of the image demonstrates how the exemplary circuit is capable of sensing the drop.

For example, in implementations of the system 100 including the temperature sensor 101a and/or the optical sensor 101b, the electronic components of the sensor unit 101 and/or other units of the system 100 can be integrated onto the outside of an existing bottle or container, as well as be embedded within the material of the bottle or container itself, e.g., during the manufacturing process of the bottle or container. For example, the flexible electronics can be integrated within an additive manufacturing framework where first the inner aspect of the nozzle, which touches the fluid, is made, followed by integration of flexible electronics, followed by fabrication of the outer nozzle. Similar procedures can also be employed in a manufacturing process to integrate the flexible electronics of system 100 into the container itself. For example, the exemplary flexible electronics of the system 100 can be embedded into the container 130 by using a 3D printing technique of the thin, flexible electronic components directly within or onto the materials that form the container or bottle. Exemplary advantages can be gained by integrating the flexible electronics into the container, including possibly eliminating the need for clinical studies of the bottle, as well as being totally indistinguishable from a normal bottle for the user. In such exemplary cases, wireless powering techniques can be used to power the integrated flexible electronics of the system 100. In other exemplary cases, the thin, flexible electronics can lie on the outside of the bottle for disposable use.

Force/Pressure Sensing

In some embodiments, the sensor unit 101 can include one or more sensors 101c to measure force and/or pressure, e.g., referred to as pressure sensors in this patent document. For example, the pressure sensors 101c can include a force sensitive resistor (FSR) or a strain gauge. In implementations of the system 100, the pressure sensor(s) 101c is placed over the body of the container 130 to detect squeezing of the container by a user. For example, a certain amount of pressure applied to (e.g., squeezed) the container 130 is required to release a certain amount of the liquid (e.g., such as a drop). The system 100 can determine the amount of pressure based on the acquired signals from the sensor unit 101 and determine if the detected amount of pressure is above or below a threshold, which can be used to infer the release of the drop, for example.

Figure 4A:
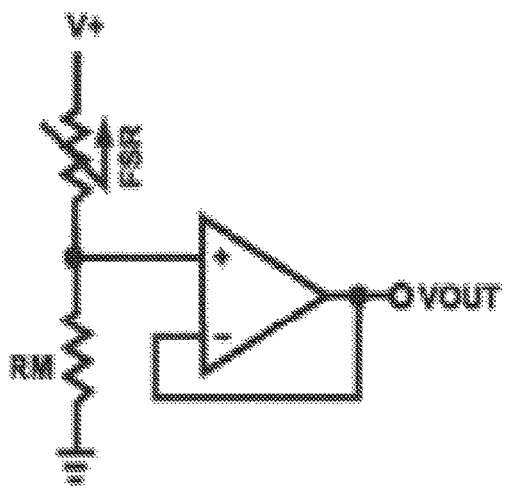
FIGS. 4A and 4B show diagrams and images of an exemplary system to monitor dispensing of a droplet using an exemplary flexible sensor unit including a force/pressure sensor attached to a droplet dispenser.
Figure 4B:
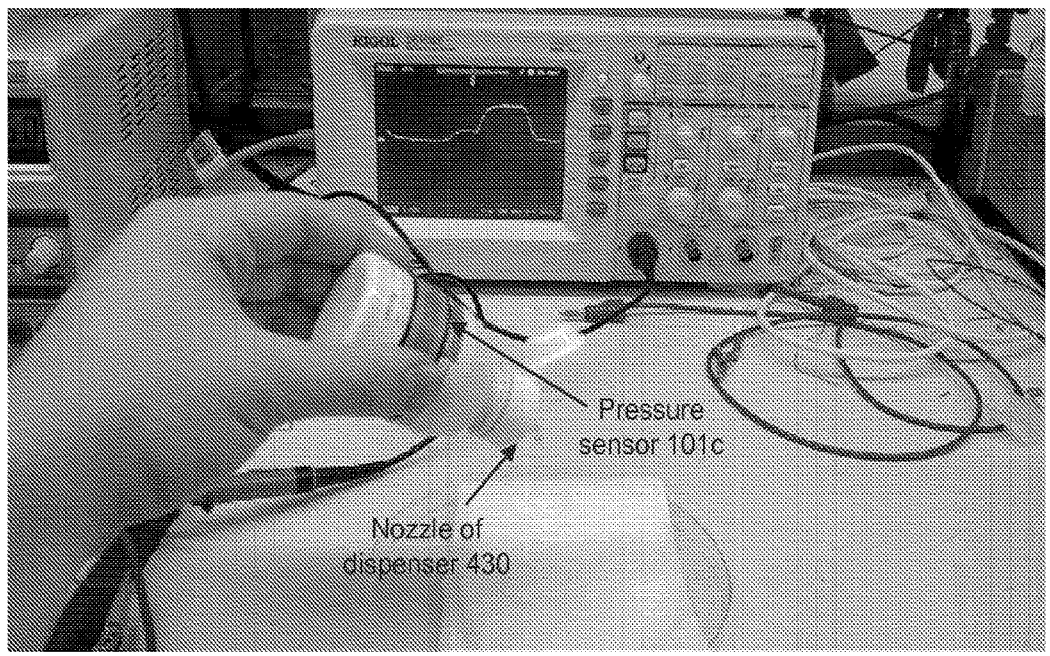

FIGS. 4A and 4B show diagrams and images of an exemplary system to monitor dispensing of a droplet using an exemplary flexible sensor unit including a pressure sensor attached to a droplet dispenser. FIG. 4A shows a diagram of an exemplary circuit, e.g., in an exemplary embodiment of the signal processing unit 105, to implement an exemplary amplification scheme using a force sensitive resistor (FSR) in the pressure sensor 101c of the system 100. FIG. 4B shows an image depicting an exemplary implementation of an exemplary force/pressure sensing embodiment of the system 100 attached to a squeezable container (e.g., a droplet dispenser) 430 including the pressure sensor unit 101c.

Figure 4C:
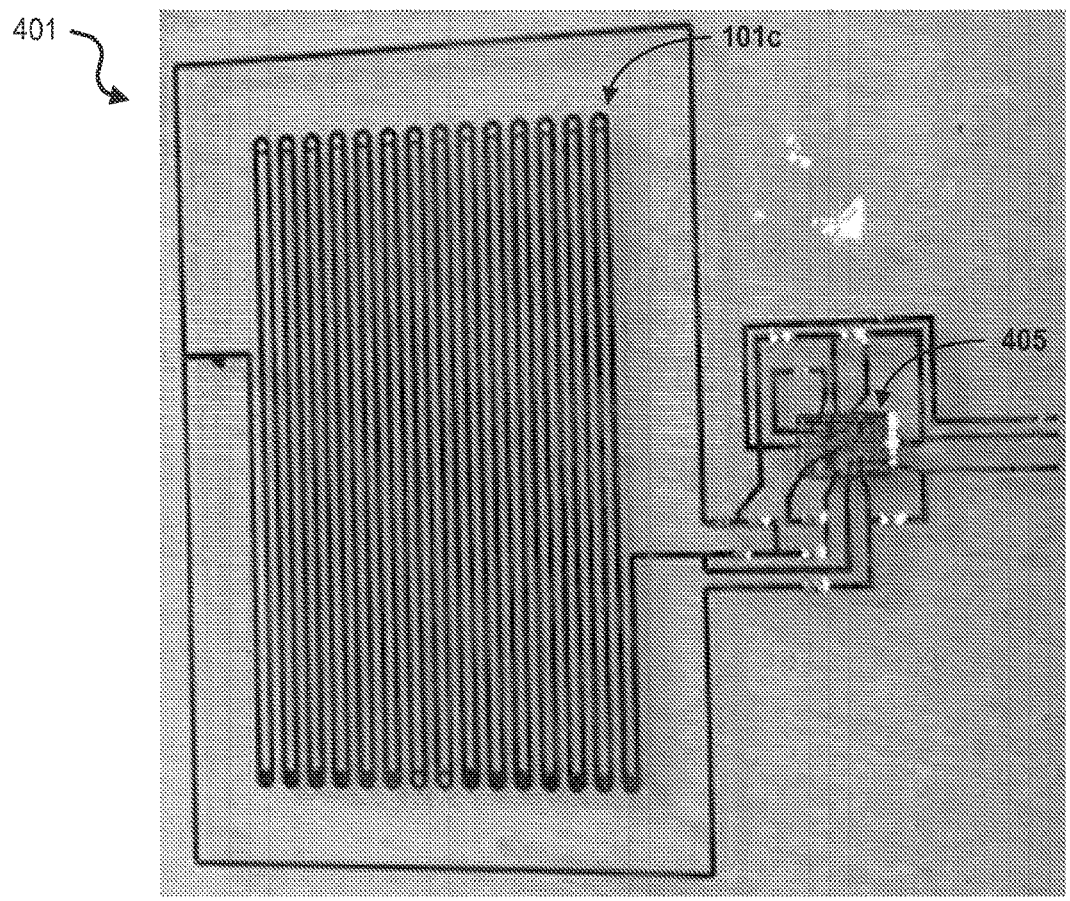
FIG. 4C shows an image of an exemplary force and/or pressure data acquisition unit of the disclosed technology.

FIG. 4C shows an image of an exemplary force and/or pressure data acquisition unit 401 of the disclosed technology. The force/pressure data acquisition unit 401 includes a flexible pressure sensor 101c (e.g., FSR) electrically coupled to a flexible signal processing circuit 405. The force/pressure data acquisition unit 401 can be unobtrusively attached to a container, e.g., such as a fluid dispensing container, or blister pack container, or other type container, to detect the dispensing of a droplet from a fluid dispensing container, or to detect the piercing or tampering of a cover (e.g., lidding stock) over a blister in a blister pack container. For example, such detected signals can be processed and used for monitoring patient compliance of a medicine container.

Figure 4D:
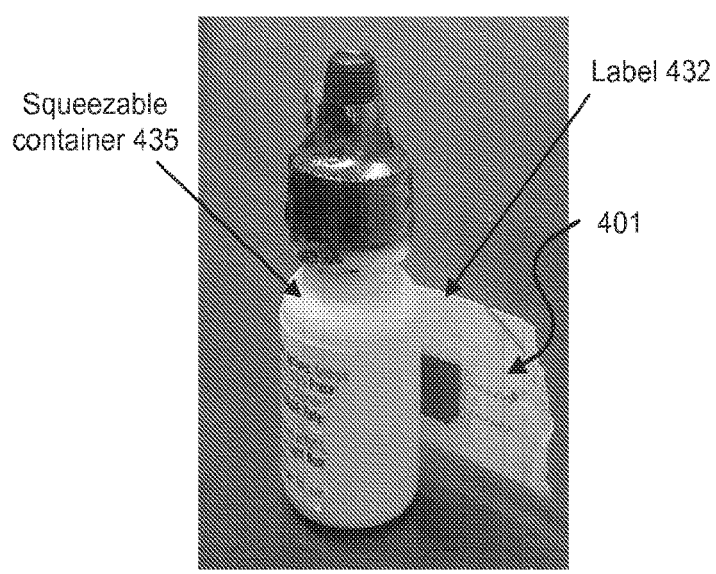
FIG. 4D shows a diagram of the exemplary force/pressure data acquisition unit integrated with a label wrapped around a squeezable container.

FIG. 4D shows a diagram of the force/pressure data acquisition unit 401 integrated with a label 432 wrapped around a squeezable container 435 (e.g., droplet bottle) for a particular medicine (e.g., eye drops). For example, a flexible electronics device or system of the disclosed technology that includes the/pressure data acquisition unit 401 can be integrated with the label 432 in a separate manufacturing process from that of the medicine in the container 435. The force/pressure data acquisition unit 401 can be attached and conformed on the container 435 after the medicine is enclosed (sealed). In some implementations, for example, the force/pressure data acquisition unit 401 can be attached to the container 435 prior to application of the label 432. Whereas in some implementations, for example, the force/pressure data acquisition unit 401 can be incorporated into the label 432 be attached to the container 435.

Figure 4E:
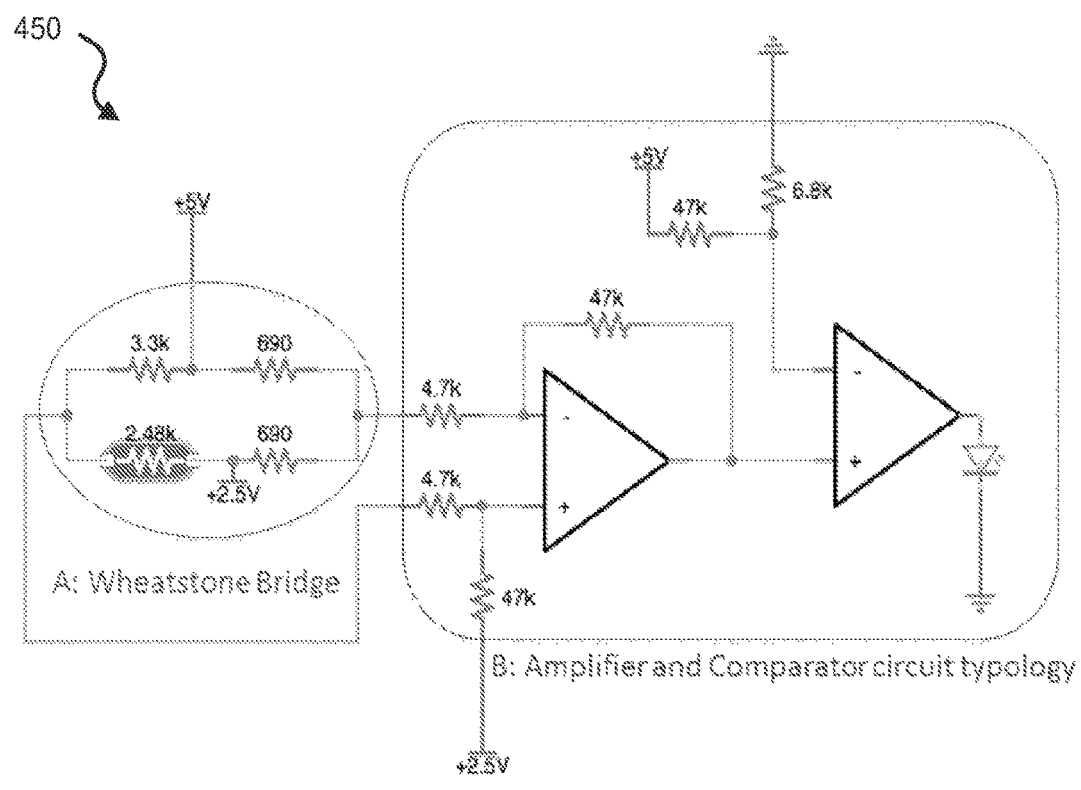
FIGS. 4E and 4F show diagrams of an exemplary flexible signal processing circuit to process detected force or pressure.
Figure 4F:
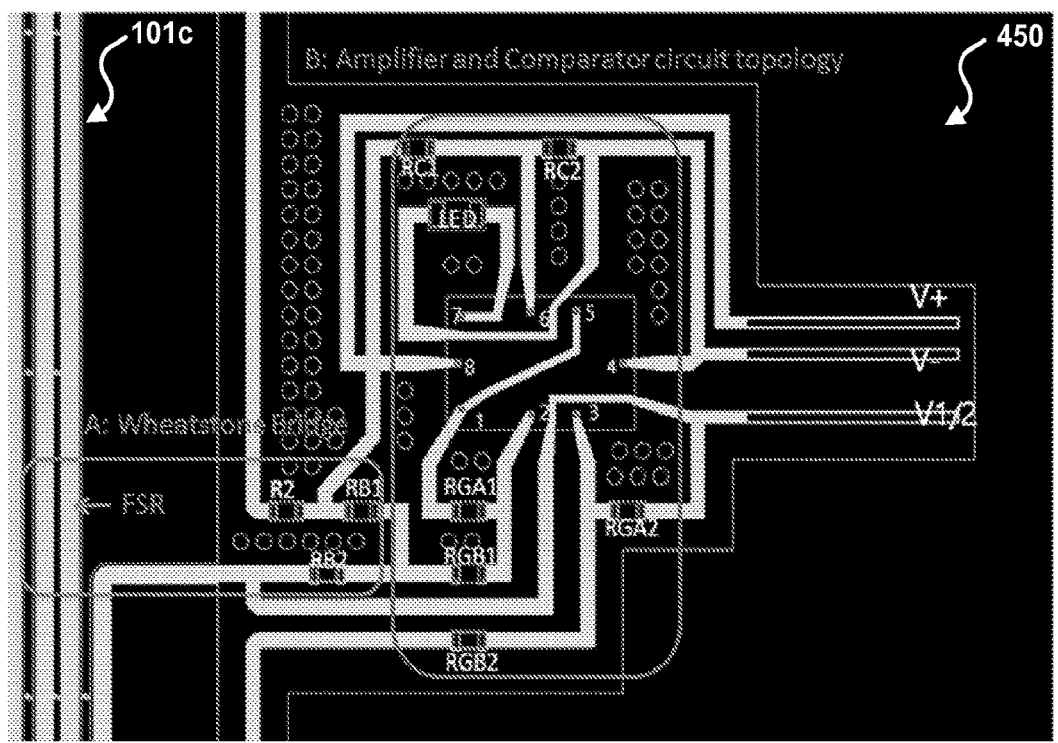

FIGS. 4E and 4F show diagrams of the exemplary flexible signal processing circuit 405 to process the detected force or pressure on the pressure sensor 101c, e.g., for monitoring use of a container. FIG. 4E shows a circuit diagram of an exemplary two stage signal processing circuit 405 including a Wheatstone bridge (e.g., stage A) and an amplifier and comparator circuit (e.g., stage B). The stage B includes an optical emitter (e.g., LED) to provide an optical signal indicative of detection of a force or pressure by the pressure sensor 101c. FIG. 4F shows a circuit diagram of the exemplary two stage signal processing circuit including a microchip including two operational amplifiers (Op Amps) in an 8-pinout configuration. For example, the exemplary two stage signal processing circuit 405 can be fabricated on the flexible and conformal substrate 102 to be bendable and/or stretchable and have a small footprint, e.g., in which the signal processing circuit 405 can be on the order of tens $mm^2$ (such as <10 mm×<10 mm dimensions).

Figure 4G:
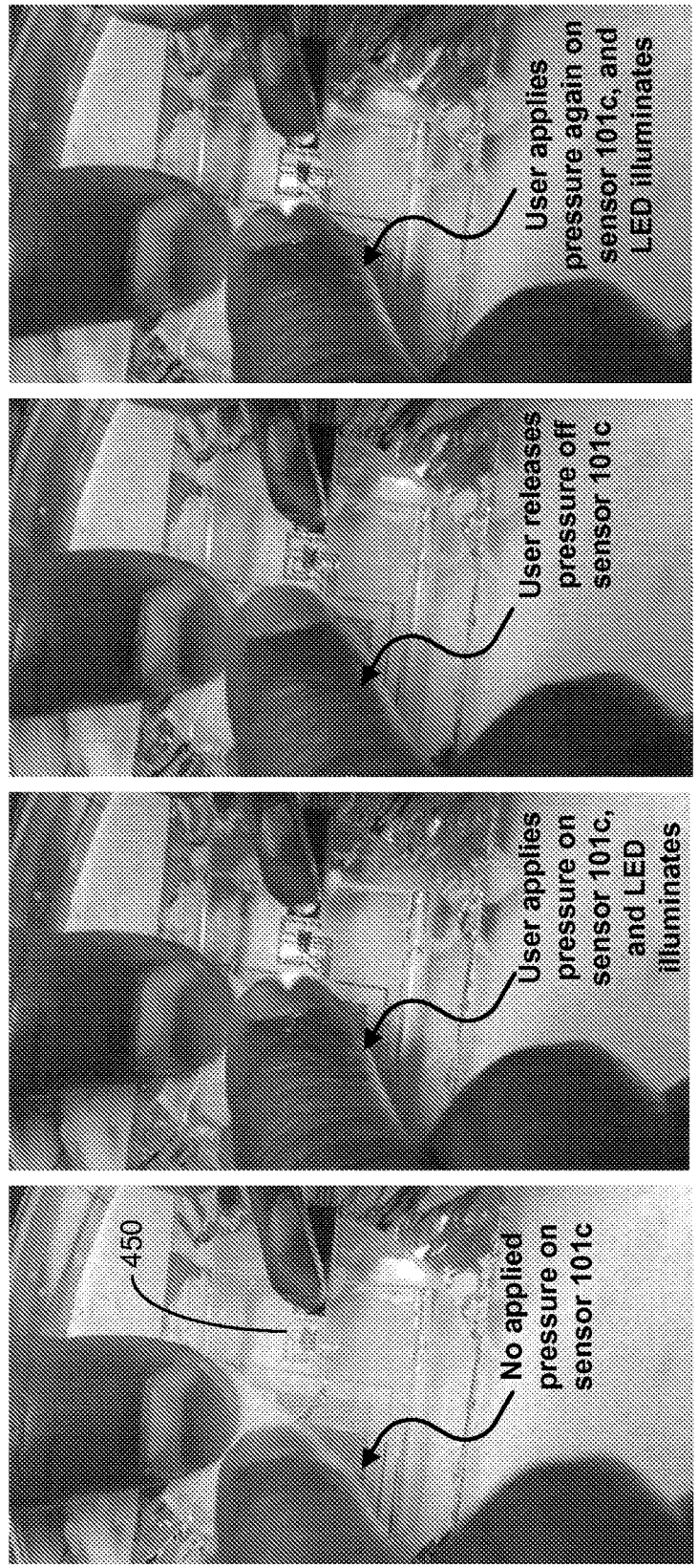
FIG. 4G shows a sequence of images depicting an implementation of the exemplary force/pressure data acquisition unit including an optional LED to indicate that force or pressure is being applied.

FIG. 4G shows a sequence of images depicting an implementation of the exemplary force/pressure data acquisition unit 401, including the optional LED to indicate that force or pressure is being applied. In the image sequence, at first (far-left image), a user is not applying any pressure onto the pressure sensor 101c (e.g., flexible FSR), which is indicated by the lack of light emitted by the signal processing circuit 450. Next (center-left image), the user applies pressure onto the pressure sensor 101c, which is indicated by a blue light emission by the LED of the signal processing circuit 450. Next (center-right image), the user releases pressure off of the pressure sensor 101c, which is indicated by the lack of light emitted by the signal processing circuit 450. Finally (far-right image), the user reapplies pressure onto the pressure sensor 101c, which is indicated by a blue light emission by the LED of the signal processing circuit 450.

In some implementations of the system 100, the force/pressure data acquisition unit 401 can be attached to a fully detachable or partially detachable lid of a container (e.g., medicine bottle) to monitor and detect the dispensing of the contents of the container by a user (e.g., detect an occurrence of when one or more pills contained in the medicine bottle are dispensed out of the medicine bottle).

Position Sensing

In some embodiments, the sensor unit 101 can include one or more position sensors 101d. For example, the position sensors 101d can include a motion sensor such as a gyroscope or an accelerometer. Implementations of the system 100 can include using the position sensor 101d in conjunction with the pressure sensor 101c in the configuration of the sensor unit 101. In one exemplary implementation, the position sensor(s) 101d is placed on a location on the container 130 to detect its orientation, and the pressure sensor(s) 101c is placed over the body of the container 130 to detect squeezing of the container by a user. If the container 130 is detected to be at a certain angular position within a particular range and the pressure threshold is determined to have been crossed, then the system 100 can determine that it is likely for a drop to have been released. For example, this determination can eliminate a false positive when the bottle is squeezed without it being positioned to dispense drops.

In some implementations of the system 100, the position sensor 101d can be attached to a fully detachable or partially detachable lid of a container (e.g., medicine pill bottle) and a second position sensor 101d can be attached to the body of the container (e.g., the pill bottle itself) to monitor and detect dispensing events of the contents of the container by a user (e.g., detect an occurrence of when the lid is detached or partially detached and oriented different from the closed setting, and with reference to the orientation of the pill bottle body, in order to infer when one or more pills contained in the medicine bottle are dispensed out of the medicine bottle). Additionally, for example, the force/pressure data acquisition unit 401 can also be attached to the body of the container (e.g., medicine pill bottle) and/or the lid to provide additional data to that of the position sensors 101d to detect the dispensing of the contents from the container.

Figure 4H:
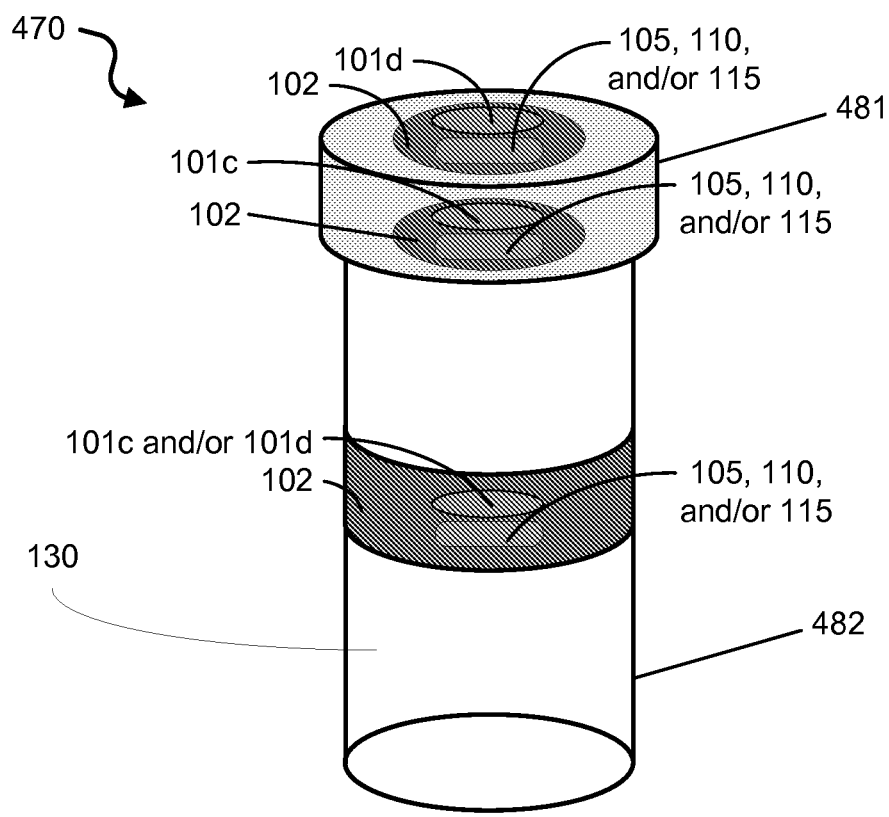
FIG. 4H shows an illustrative diagram of an exemplary pressure and position data acquisition unit of the disclosed technology unobtrusively attached to a container having a detachable lid to detect the dispensing of the contents from the container.

FIG. 4H shows an illustrative diagram of an exemplary pressure and position data acquisition unit 470 of the disclosed technology unobtrusively attached to a container having a detachable lid to detect the dispensing of the contents from the container, e.g., in which the detected dispensing data can be processed for monitoring patient compliance. As shown in the diagram of FIG. 4H, the position sensor 101c is attached to or integrated in the conformal substrate 102 of the system 100 that is attachable to a detachable or partially detachable lid 481 of the container 130, e.g., such that the system 100 is inconspicuously integrated with the lid 481. The pressure sensor 101d may alternatively or additionally be attached to or integrated in the conformal substrate 102 of the system 100 (e.g., either a separate substrate or the same substrate portion) that is attachable to the lid 481. An additional data acquisition unit 101 may be employed on the body 482 of the container 130. In the exemplary embodiment shown in FIG. 4H, the pressure sensor 101c and/or the position sensor 101d is attached to or integrated in the conformal substrate 102 of the system 100 that is attachable to the body 482 of the container 130. The pressure and position data acquisition unit 470 is configured such that if a user squeezes the fully or partially detachable lid 481 to open the lid (and/or squeezes or changes the orientation of the body 482), the user's applied force or pressure and/or the change in orientation of the lid 481 (and/or the body 482) can be detected to indicate a dispensing event. The pressure and position data acquisition unit 470 is in communication with the signal processing circuit 105, e.g., which can amplify and/or modulate the detected signal for data processing by the data acquisition unit 110, and/or for transmission to the device 120 by the wireless communication unit 115. In addition, or alternatively, for example, the optical sensor 101b and/or the temperature sensor 101a can be configured at the opening of the body 482 to detect dispensing of the contents (e.g., fluid or pills) from the body 482 of the container 130.

The disclosed flexible electronics units of the system 100 can be fabricated using flexible electronics device fabrication techniques. The disclosed flexible electronic units of the system 100 can be embedded into the container 130 by using 3D printing methods that form the thin, flexible electronic components directly onto the materials that form the container or bottle. In one example, a base material can be created by 3D printing fabrication that produces an inner material layer that forms the interior portion of the bottle or container having an interior chamber that holds the fluid within. Subsequently, the exemplary flexible electronics units of the system 100 (e.g., such as the sensor unit 101, the signal processing unit 105, the data processing unit 110, and/or the wireless communications unit 115) can be 3D printed on the base material, e.g., at a particular location on the based material. For example, in some implementations, the exemplary flexible electronic units can be 3D printed on a conformal substrate including a mechanically flexible and an electrically insulative material that is attached to the inner material layer. Subsequently, an outer material can be created by 3D printing fabrication that produces an exterior material layer over the flexible electronics units of the system 100 to integrate them within the container or bottle structure. For example, the outer and base materials can be created with a shape, size, and/or geometry to form the container or bottle structure; or in some implementations, further material layers and structures can be added (e.g., using 3D printing) to produce the overall structure of the container with the integrated system 100 within the container structure. In some device fabrication implementations, for example, the disclosed flexible electronics units of the system 100 can be fabricated and embedded into the container, e.g., using injection molding techniques. For example, the flexible electronics can be placed inside a mold and an insulating polymer material that is compatible can be injected into the mold.

Exemplary Software Application

Exemplary feedback schemes to assist in patient compliance of using a medication by a bottle implementing the disclosed systems are described. In one example, using a wireless connection (e.g., Bluetooth) between a user's smartphone as an example of the mobile device 120 and the container 130 having the system 100 attached, the system 100 can log the release timing of a drop from the container 130 on the smartphone and issue reminders for the patient to take their medication and/or indicate when the patient forgets.

The disclosed technology can include a software application resident on the user's mobile device 120 and/or computing device(s) of the same or other users, e.g., such as caregivers to the patient user, to manage information associated with the detected use of the container by the user (e.g., detected droplet dispensing, container cap removal, or puncture/peeling of cover over blister). For example, the software application can provide an interface for a user (e.g., the patient, caregiver, or other type of user) to access information about their usage of the contents inside the container having the system 100 applied to it, e.g., providing temporal usage information on the day and time that the contents was released from the container (e.g., a droplet, pill, or dosage of a medication was taken by the patient). For example, the information provided via the software application can include a percentage of medicine taken (e.g., percentage of drops taken) within a specified time window, e.g., which can be important for clinicians or other care providers to determine if the effect of a medical condition (e.g., an eye condition) worsening is due to infeasibility of the current intervention or due to lack of compliance. The software application can allow tracking of when an amount of medicine was taken (e.g., droplet dispensed, or pill removed from a container vial or blister pack), and the software application can provide alerts or messages to users (e.g., the patient, caregiver, or other intended user) to notify the patient user to take the medicine and/or notify the caregiver that the user has or has not taken the medicine (e.g., for a particular time or time period). The software application can provide such alerts and notifications by sending displaying a notification on the display screen of the mobile device 120, sending a text message to the user(s), and/or transmitting command data from the mobile device 120 to the system 100 on the container 130 to provide an alert signal (e.g., light an LED (e.g., blinking or a color coded illumination), sound an audio alarm via a speaker, and/or cause a haptic response).

The software application can process the data received from the system 100 to determine if multiple doses (e.g., drops) were taken in a single suggested dosing interval. Such information can be used by caregivers to understand other challenges for the patient in compliance with the prescribed regimen. Moreover, such dose tracking (e.g., droplet dispensing, or pill dispensing) information can be processed by the software application to determine how much medicine may be remaining in the medicine container. As such, the software application can estimate when the patient should be finished with the medicine in that particular container (e.g., when the container will be emptied), and act on the estimated information. For example, the software application can provide notification to the patient or caregiver to contact the pharmacy or physician for refill of the medication, or the software application can automatically inform the pharmacy or physician to refill the medication. By accurately tracking the usage (e.g., droplets), the software application can mitigate risks to prevent the patient from being out of supply of their medication and not miss any dosage.

For example, many eye medications include droplet products that are for the elderly and aging population, who may suffer from diminishing manual dexterity. The software application can provide information to caregivers on the patient's ability to squeeze and/or aim the medicine container including the system 100 having the pressure sensor and/or position sensor units. Moreover, some patients (e.g., including elderly patients) may be taking one or more other medications for conditions that may be associated with diminishing dexterity (e.g., Parkinson's Disease). For example, suppose a patient with Parkinson's Disease and an eye condition requiring droplet medication takes the Parkinson's Disease medicine on certain days or certain times per day. The tracking of the patient's ability to manage the squeezing and aiming of the eye medication container having the system 100 may play a role in providing useful information to a caregiver regarding the patient's other condition, e.g., Parkinson's Disease. The software application can be used to integrate information across multiple different medication types and then help the understanding of their efficacy. For example, a container vial with a detachable lid or a blister pack having the system 100 can provide information to the caregiver via the software application that characterizes when the patient takes a swallowable pill whose effect can correlate with the effect of the droplet medication being tracked—this information is actionable. The information about the multiple medications is important to be displayed and statistically quantified for the purpose of improved decision support. By integrating that data and correlating dosage across suggested dosage, within a specific medication as well as across, a caregiver can better understand the efficacy of the medication.

The software application can process the data received from the system 100 to monitor security and safety related issues associated with the medication contained in the container 130. For example, software application can process the data received from the system 100 to determine if multiple doses (e.g., drops or pills) were taken in a particular dosing interval to indicate potential abuse of the medication. For example, the software application can include data processing methods that identify potential substance addiction behavior. For example, if the software application can process the detection data to identify instances and/or patterns of use that are inconsistent with a predetermined pattern of use (e.g., prescription is for one pill or droplet per day, to be taken at night). Such identified instances can be reported to the caregiver or other entities. Similarly, the software application can provide location data associated with the detection of the dispensing occurrence(s) and/or quantity of dispensing. For example, in some embodiments, the data processing unit 110 of the system 100 can include a location positioning unit to determine the location of the system 100. For example, in some implementations, the location positioning unit can include a GPS device. In some implementations, for example, the system 100 can include location processing techniques to determine an approximate location of the system based on communications between the wireless transmitting unit 115 and remote devices (e.g., WiFi transmitter/receiver). In some implementations, for example, the software application can notify certain entities (e.g., the patient, caregivers, etc.) if one or more dispensing events have occurred based on data stored in memory of the data processing unit 110 without associated communications of those dispensing events from the system 100 to the user's mobile device 120, e.g., where such instances could be indicative of an improper use of the medicine in the container 130.

Figure 5A:
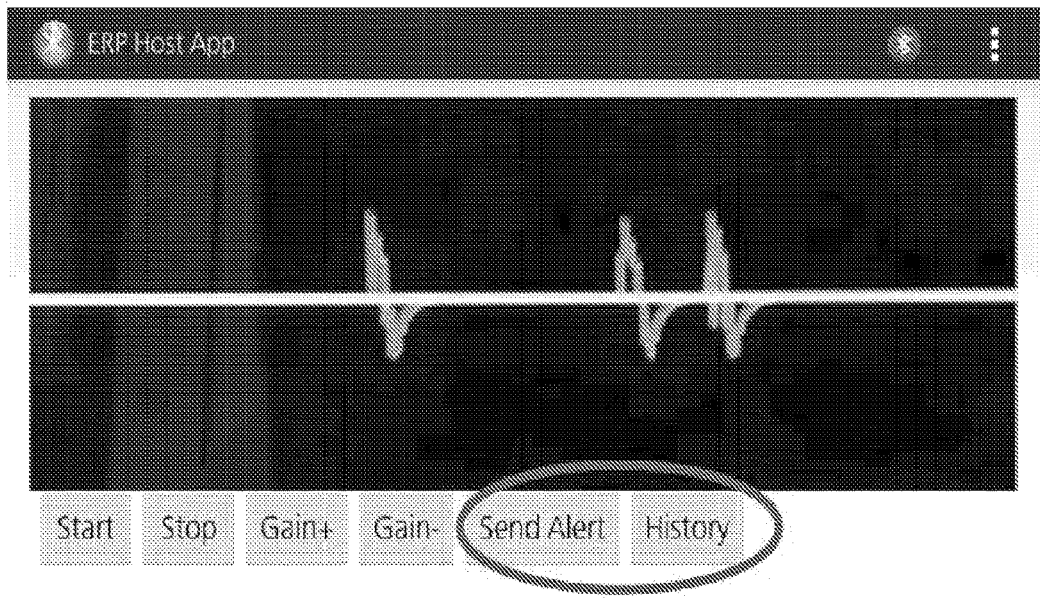
FIGS. 5A-5C show diagrams of an example user interface of a software application of the disclosed technology.
Figure 5B:
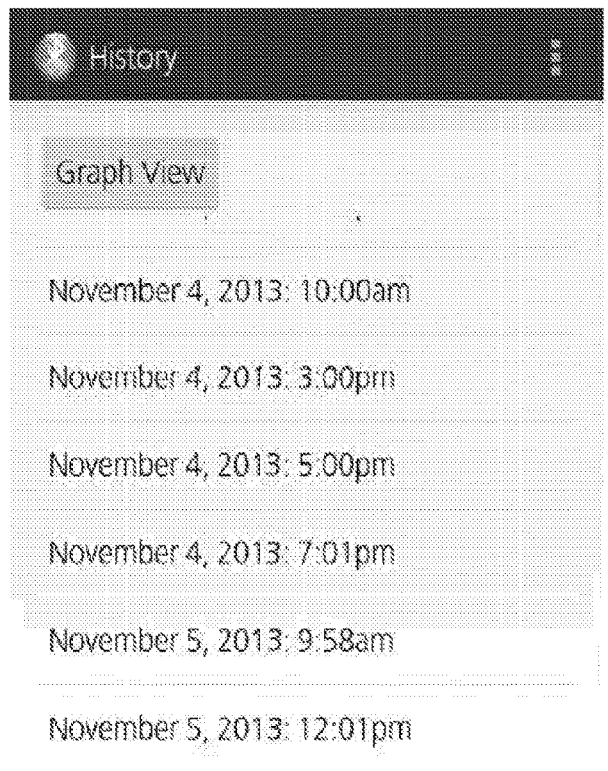
Figure 5C:
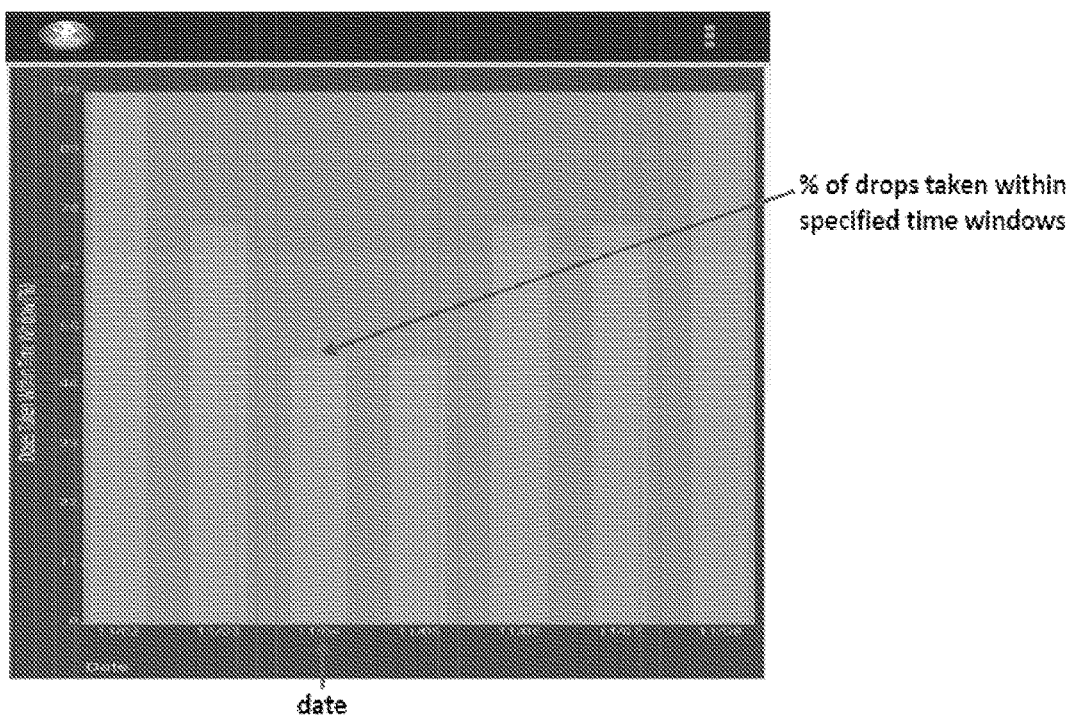

FIG. 5A shows a screen shot diagram of an example user interface of an exemplary software application of the disclosed technology resident on the mobile device 120, showing a time response of droplet administration detected by the system 100 on an example droplet dispenser. FIG. 5B shows a screen shot diagram of an example interface showing a time history of the medicine administration (e.g., dispensed droplets) performed by a user detected by the disclosed flexible electronics devices. FIG. 5C shows a screen shot diagram of an example interface showing a percentage time history of medicine administration in a given time period performed by the user detected by the disclosed technology.

Figure 6:
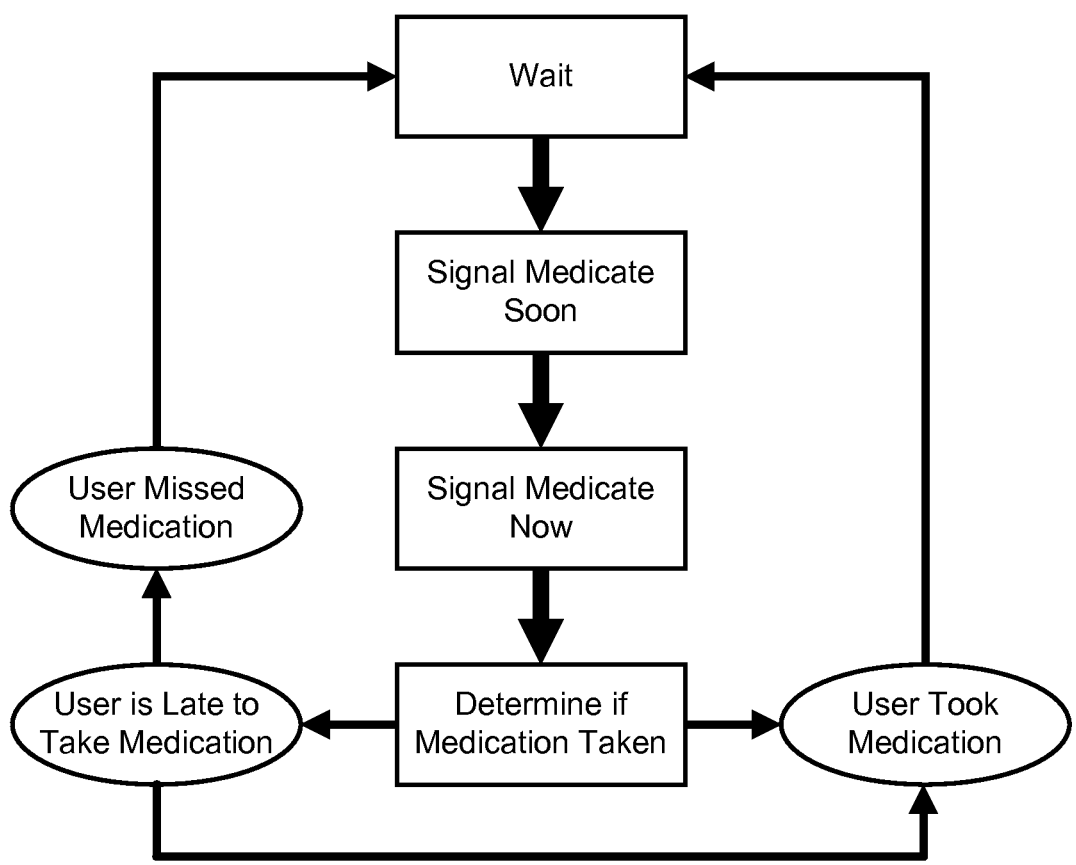
FIG. 6 shows a flow diagram of an exemplary feedback method to facilitate patient compliance in taking a medication using a bottle incorporating an exemplary flexible electronic monitoring system of the disclosed technology.

In another example, an internal timer on the bottle can be set for an optimal dosage time. At a set interval prior to this time, the bottle illuminates to indicate that it is almost time to medicate. During the optimal medication window, the bottle changes states (e.g., a change in color or blinking in the lights) to indicate that the medicine should be taken. If the medicine was taken, for example, the bottle changes states again to indicate the medicine was taken. If the medicine was not taken within the optimal medication window, for example, the bottle will change state to indicate that the dose was missed or late. Each state can be logged to internal memory of the data processing unit 110 or a memory unit of a remote computer and extracted later to check patient compliance. This exemplary second feedback scheme is depicted in the flow diagram of FIG. 6. FIG. 6 shows a flow diagram of an exemplary feedback method to facilitate patient compliance in taking a medication using a bottle incorporating an exemplary flexible electronic monitoring system of the disclosed technology.

The disclosed approach uses ultra-thin flexible electronics that remain unobtrusive to a user by inserting into or wrapping them around a container, e.g., such as a bottle. In some examples, the flexible electronic components that are used in the various embodiments of the system 100 can be produced by using bare die chips integrated into flexible polymer substrates (e.g., polyimide or elastomers). For example, such techniques can take existing small chip components and integrate into a flexible electronics solution. Such fabrication techniques can provide flexible electronics systems and devices, as described in this patent document, to allow for an ergonomic sensing container or bottle that can be utilized in a variety of ways, e.g., including monitoring and intervening in patient compliance for use of a medication or other substance.

Exemplary Blister Pack Embodiments

In some aspects, the disclosed flexible electronic sensor and wireless communication technology can integrate directly into blister pack configurations of medical dispensers, or other type of dispensers, to infer the release of the contents (e.g., medication) from the blister pack. The disclosed flexible electronics devices and systems combine sensing logic and wireless communication capabilities to facilitate patient compliance through monitoring of medication dispensing in time. Such flexible electronics devices and systems of the disclosed technology can be incorporated into existing non-electronic blister packs through additive post-processing, in which the flexible electronics system can be built independently and attached directly to the frangible backing of a blister pack in its current off-the-shelf state, thus providing a simple 'two-step' manufacturing method of electronic blister packs.

Existing patient compliance systems are obtrusive and typically require manufacturing of new medical dispensers to enable monitoring of patient compliance. Moreover, these conventional systems can require burdensome procedures to extract monitored information (e.g., such as non-wireless or non-automated measures), which may even cause non-compliance. In contrast, the disclosed flexible electronic sensor and wireless communication technology includes designs that can be produced in an additive manner and that have no obtrusive features that could interfere with patient compliance.

Figure 7:
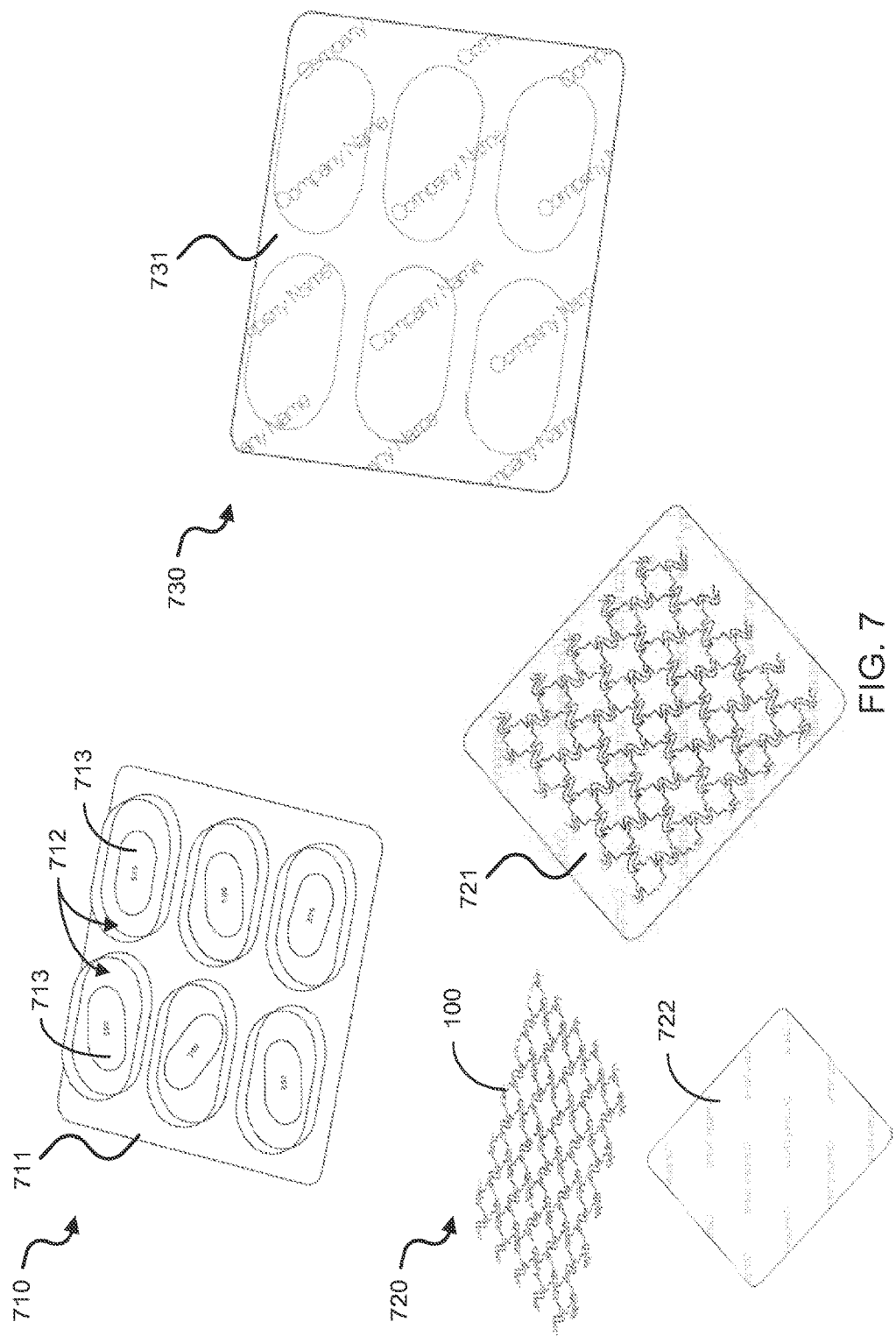
FIG. 7 shows an illustrative diagram of a method to produce a blister pack container including an exemplary flexible electronics system of the disclosed technology.

In some examples, the disclosed technology includes an embodiment of the system 100 included in a frangible sheet that can be attached to a blister pack container pre-filled with medicine, where the frangible sheet and coupled system 100 are attached to the blister pack container after the medicine is sealed and secured, and in which the system 100 can unobtrusively monitor the release of each medication from the blister pack container. FIG. 7 shows an illustrative diagram of a method to produce a blister pack container including the system 100.

As shown in FIG. 7, process 710 includes the fabrication of a blister pack container 711 including blister troughs 712 to contain the manufactured medication 715, e.g., pills already dispensed within the blister pack container base 711. The container base 711 can include a sealant layer attached over the blister troughs 712 that enclose and seal the medication 713 inside (e.g., such as a frangible paper backing laminated onto a foil backing, much like a label on existing commercial blister pack containers). Process 720 includes the fabrication of a frangible backing 721 for the blister pack container 711 that includes the system 100 (e.g., such as the system 100 including the force/pressure data acquisition unit 401) on a substrate 722 of the frangible backing 721. The frangible backing 721 includes a mounting side that includes the system 100 and an adhesive to attach to the pre-filled and pre-sealed blister pack container base 711. In some implementations, for example, the frangible backing 721 can include labeling or messaging on the outer side of the frangible backing 721. The process 710 and the process 720 can be implemented separately and are independent from each other. Process 730 includes the combination of the medication-filled blister pack container 711 and the frangible backing 721 including the system 100 to form a smart blister pack medicine container 731 capable of patient compliance. For example, the process 730 includes attaching the mounting side of the frangible backing 721 to the sealed layer of the blister pack container 711. In some implementations, for example, the attachment of the backing 721 to the blister pack 711 can be performed by laminating or other attachment processes. The flexible electronic device 100 is not seen, but is operable to detect peeling off of or puncture through of the frangible backing 721 over each one of the several blister troughs 712.

Figure 8:
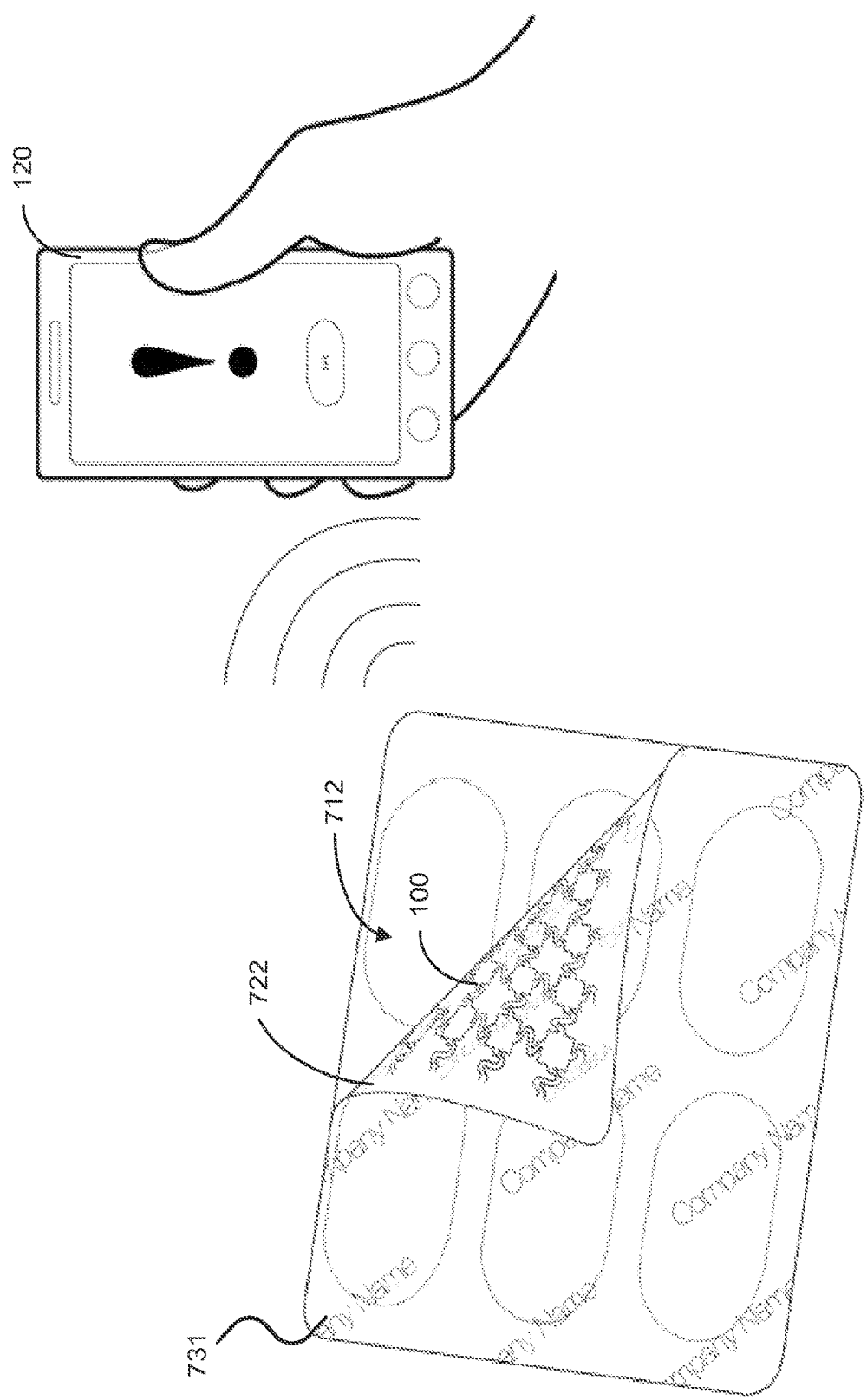
FIG. 8 shows an illustrative diagram of a patient using a smart blister pack medicine container of the disclosed technology.

FIG. 8 shows an illustrative diagram of a patient using the smart blister pack medicine container 731 to peel off a portion of the frangible backing 721 (e.g., to access a pill pre-sealed in the blister trough 712), in which the system 100 is able to detect the user's peeling of the frangible backing 721 to transmit the detected data to the user's mobile device 120.

While several of the disclosed embodiments that are described in this patent document are primarily based on monitoring the dispensing of medicine from a medicine container (e.g., such as droplet dispenser, pill bottle with detachable lid, and blister pack) to facilitate understanding of the underlying concepts of the disclosed technology, it is understood that the disclosed devices, systems, and methods can also include monitoring of other contents and substances in similar type containers, which include, but are not limited to, foods, drinks and food-related products (e.g., vitamins, nutrient supplements, gum, candy), nicotine delivery products (e.g., nicotine gum), and non-consumable products.

Examples

The following examples are illustrative of several embodiments of the present technology. Other exemplary embodiments of the present technology may be presented prior to the following listed examples, or after the following listed examples.

In one example of the present technology (example 1), a device for monitoring patient compliance of a medication includes a substrate that is attachable and conformable to a container containing medicine; a data acquisition unit including a sensor and a signal processing circuit formed on the substrate, in which the sensor is operable to transduce an occurrence of the medicine dispensing from the container into an electrical signal, and the signal processing circuit is operable to amplify the electrical signal; a data processing unit including a processor and a memory formed on the substrate and in communication with the data acquisition unit to process the amplified electrical signal as data; and a communications unit formed on the substrate and in communication with the data processing unit to wirelessly transmit the processed data to a remote device.

Example 2 includes the device as in example 1, in which the substrate includes a mechanically flexible and an electrically insulative material.

Example 3 includes the device as in example 1, in which the device is capable to inconspicuously attach to the container.

Example 4 includes the device as in example 1, in which the container includes a droplet bottle, a blister pack, or a bottle with a detachable lid.

Example 5 includes the device as in example 1, in which the data processing unit is configured to determine an amount of the medicine dispensed from the container based on the electrical signal.

Example 6 includes the device as in example 1, in which the processed data indicates a time at which the determined dispensing event occurred.

Example 7 includes the device as in example 6, in which the data processing unit is configured to determine if the time at which the determined dispensing event occurred is before or after a predetermined time.

Example 8 includes the device as in example 7, in which the data processing unit is configured to produce a message indicating the dispensing event was early or late based on the predetermined time.

Example 9 includes the device as in example 1, in which the sensor includes one or more of a temperature sensor, an optical sensor, a pressure sensor, or a position sensor.

Example 10 includes the device as in example 9, in which the medicine includes a fluid, and the substrate is attached and conformed at or proximate to a nozzle of the container.

Example 11 includes the device as in example 10, in which the temperature sensor includes a temperature dependent resistive flow sensor operable to produce the electrical signal by detecting a temperature fluctuation when the fluid passes out of the nozzle.

Example 12 includes the device as in example 10, in which the optical sensor includes a light emitting diode (LED) positioned at one end of the nozzle and a photodetector positioned at an opposing end of the nozzle to receive light emitted by the LED, in which the optical sensor is operable to produce the electrical signal by detecting, at the photodetector, a change in a refraction index of the emitted light caused when the fluid passes out of the nozzle.

Example 13 includes the device as in example 9, in which the medicine includes a fluid, and the substrate is attached and conformed to the body of the container.

Example 14 includes the device as in example 13, in which the pressure sensor includes a force sensitive resistor (FSR) or a strain gauge, in which the pressure sensor is operable to produce the electrical signal corresponding to an amount of pressure change caused by squeezing the body of the container.

Example 15 includes the device as in example 14, in which the data processing unit is operable to determine if the detected amount of pressure is above or below a threshold value to determine the occurrence of the dispensing event.

Example 16 includes the device as in example 9, in which the position sensor includes a gyroscope or an accelerometer, in which the position sensor is operable to produce the electrical signal based on a change in orientation of the container detected by the position sensor.

Example 17 includes the device as in example 1, further including an LED electrically coupled to the signal processing circuit and operable to emit a light when the sensor detects the occurrence of the medicine dispensing from the container.

Example 18 includes the device as in example 1, further including an alert unit including one or more of an LED, a speaker, or a vibrator in communication with the data processing unit to generate an alert signal from the container.

Example 19 includes the device as in example 18, in which the data processing unit is operable to determine compliance of a user of the container for taking the medicine according to a schedule of use for the user, and to produce a command signal to actuate the alert unit to generate the alert signal when the dispensing event was early or late based on the schedule of use.

In another example of the present technology (example 20), a method for monitoring dispensing of medicine from a container includes detecting a signal by a sensor on a conformal substrate attached and conformed to a container containing medicine; and processing the detected signal to produce data indicative of an occurrence or a non-occurrence of the medicine dispensed from the container.

Example 21 includes the method as in example 20, in which the conformal substrate includes a mechanically flexible and an electrically insulative material, and in which the sensor includes one or more of a temperature dependent resistive flow sensor, an optic flow sensor, a pressure sensor, or a position sensor.

Example 22 includes the method as in example 20, in which the detecting includes transducing events corresponding to the medicine dispensing and not dispensing from the container into distinguishable electrical signals, and amplifying the electrical signals.

Example 23 includes the method as in example 20, in which the processing includes determining an amount of the medicine dispensed from the container based on the detected signal.

Example 24 includes the method as in example 20, in which the processing includes associating a time value with a determined occurrence.

Example 25 includes the method as in example 24, in which the processing includes determining if the time value associated with the determined occurrence is before or after a predetermined time.

Example 26 includes the method as in example 20, in which the processing is performed by a data processing unit on the conformal substrate.

Example 27 includes the method as in example 26, further including wirelessly transmitting the processed data to a remote device.

Example 28 includes the method as in example 27, further including producing an alert corresponding to a message indicating a dispensing event is upcoming, a dispensing event has occurred, or a dispensing event has been missed.

Example 29 includes the method as in example 20, further including determining compliance of a user using the medicine according to a particular schedule of use for the user.

Example 30 includes the method as in example 29, further including generating a message indicating the dispensing event was early or late based on the predetermined time.

Example 31 includes the method as in example 20, in which the container includes a droplet bottle, a blister pack, or a bottle with a detachable lid.

In another example of the present technology (example 32), a device for monitoring dispensing of a fluid from a container includes a data acquisition unit including a sensor and a signal processing circuit formed in a material structure of a container capable of storing and dispensing a fluid, in which the sensor transduces an occurrence of the fluid dispensing from the container into an electrical signal, and the signal processing circuit amplifies the electrical signal; a data processing unit including a processor and a memory unit, the data processing unit formed in the material structure of the container and in communication with the data acquisition unit to process the amplified electrical signal as data to determine a dispensing event of the fluid from the container; and a communications unit formed in the material structure of the container and in communication with the data processing unit to wirelessly transmit the processed data to a remote device.

Example 33 includes the device as in example 32, in which the data acquisition unit, the data processing unit, and the communications unit are formed in the material structure of the container by a 3D printing process.

Example 34 includes the device as in example 32, in which the container includes a droplet bottle or a bottle with a detachable lid.

Example 35 includes the device as in example 32, in which the sensor includes one or more of a temperature sensor, an optical sensor, a pressure sensor, or a position sensor.

Example 36 includes the device as in example 32, in which the sensor is configured at or proximate to a nozzle of the container in the material structure.

Example 37 includes the device as in example 36, in which the temperature sensor includes a temperature dependent resistive flow sensor operable to produce the electrical signal by detecting a temperature fluctuation when the fluid passes out of the nozzle.

Example 38 includes the device as in example 36, in which the optical sensor includes a light emitting diode (LED) positioned at one end of the nozzle and a photodetector positioned at an opposing end of the nozzle to receive light emitted by the LED, in which the optical sensor is operable to produce the electrical signal by detecting, at the photodetector, a change in a refraction index of the emitted light caused when the fluid passes out of the nozzle.

Example 39 includes the device as in example 32, in which the sensor is configured in the body of the container in the material structure.

Example 40 includes the device as in example 39, in which the pressure sensor includes a force sensitive resistor (FSR) or a strain gauge, in which the pressure sensor is operable to produce the electrical signal corresponding to an amount of pressure change caused by squeezing the body of the container.

Example 41 includes the device as in example 39, in which the position sensor includes a gyroscope or an accelerometer, in which the position sensor is operable to produce the electrical signal based on a change in orientation of the container detected by the position sensor.

In another example of the present technology (example 42), a device for monitoring dispensing from a container includes a substrate that is attachable and conformable to a container; a data acquisition unit including a sensor and a signal processing circuit formed on the substrate, in which the sensor is operable to transduce an occurrence of a content contained in the container dispensing from the container into an electrical signal, and the signal processing circuit is operable to amplify the electrical signal; and a communications unit formed on the substrate and in communication with the signal processing circuit to wirelessly transmit the amplified electrical signal to a remote device.

Example 43 includes the device as in example 42, in which the substrate includes a mechanically flexible and an electrically insulative material.

Example 44 includes the device as in example 42, further including a data processing unit including a processor and a memory formed on the substrate, in which the data processing unit is in communication with the data acquisition unit to process the amplified electrical signal as data, and in communication with the communications unit to provide the processed data to be wirelessly transmitted to the remote device.

Example 45 includes the device as in example 42, in which the sensor includes a temperature sensor positioned at an opening of the container and operable to produce the electrical signal by detecting a temperature fluctuation when the content passes out of the opening of the container.

Example 46 includes the device as in example 42, in which the sensor includes an optical sensor including a light emitting diode (LED) positioned at one end of an opening of the container and a photodetector positioned at an opposing end of the opening to receive light emitted by the LED, in which the optical sensor is operable to produce the electrical signal by detecting, at the photodetector, a change in the emitted light caused when the contents passes out of the opening of the container.

Example 47 includes the device as in example 42, in which the sensor includes a force or pressure sensor operable to produce the electrical signal corresponding to an amount of pressure change applied on a portion of the container where the sensor is attached.

Example 48 includes the device as in example 42, in which the sensor includes a position sensor operable to produce the electrical signal based on a change in orientation of the container detected by the position sensor.

The additional following examples are also illustrative of several embodiments of the present technology. Other exemplary embodiments of the present technology may be presented prior to the following listed examples, or after the following listed examples.

In one example of the present technology (example A1), a method for monitoring dispensing of a fluid from a container includes detecting a signal by a sensor on a conformal substrate attached and conformed to a container containing a fluid; processing the detected signal as data using a processing unit on the conformal substrate, the processing including determining occurrences and non-occurrences of the fluid dispensed from the container, and associating a time value with the determined occurrence; and wirelessly transmitting the processed data to a remote device.

Example A2 includes the method as in example A1, in which the detecting includes transducing events corresponding to the fluid dispensing and not dispensing from the container into distinguishable electrical signals, and amplifying the electrical signals.

Example A3 includes the method as in example A1, in which the processing further includes determining an amount of the fluid dispensed from the container based on the detected signal.

Example A4 includes the method as in example A1, in which the processing further includes determining if the time value associated with the determined occurrence is before or after a predetermined time.

Example A5 includes the method as in example A4, further including producing raw message data corresponding to a message indicating the occurrence was early or late based on the predetermined time; and transmitting the message data to the remote device.

Example A6 includes the method as in example A1, further including determining compliance of a user using the fluid according to a particular schedule of use.

Example A7 includes the method as in example A1 or A6, in which the fluid includes a medicine.

Example A8 includes the method as in example A1 or A7, in which the container includes an eye drop bottle.

Example A9 includes the method as in example A1, in which the conformal substrate includes a mechanically flexible and an electrically insulative material.

Example A10 includes the method as in example A1, in which the sensor includes one or more of a temperature dependent resistive flow sensor, an optic flow sensor, a pressure sensor, or a position sensor.

In another example of the present technology (example A11), a system for monitoring dispensing of a fluid from a container includes a conformal substrate including a mechanically flexible and an electrically insulative material, the conformal substrate attached and conformed to a container containing a fluid; a data acquisition unit including a sensor and a signal processing circuit formed on the conformal substrate, in which the sensor transduces an occurrence of the fluid dispensing from the container into an electrical signal, and the signal processing circuit amplifies the electrical signal; a data processing unit including a processor and a memory unit, the data processing unit formed on the conformal substrate and in communication with the data acquisition unit to process the amplified electrical signal as data to determine a dispensing event of the fluid from the container; and a communications unit formed on the conformal substrate and in communication with the data processing unit to wirelessly transmit the processed data to a remote device.

Example A12 includes the system as in example A11, in which the data processing unit is configured to determine an amount of the fluid dispensed from the container based on the electrical signal.

Example A13 includes the system as in example A1, in which the processed data indicates a time at which the determined dispensing event occurred.

Example A14 includes the system as in example A13, in which the data processing unit is configured to determine if the time at which the determined dispensing event occurred is before or after a predetermined time.

Example A15 includes the system as in example A14, in which the data processing unit is configured to produce a message indicating the dispensing event was early or late based on the predetermined time.

Example A16 includes the system as in example A11 or A15, in which the fluid includes a medicine.

Example A17 includes the system as in example A11 or A16, in which the container includes an eye drop bottle.

Example A18 includes the system as in example A11, in which the sensor includes one or more of a temperature dependent resistive flow sensor, an optic flow sensor, a pressure sensor, or a position sensor.

Example A19 includes the system as in example A18, in which the conformal substrate is attached and conformed on or proximate to a nozzle of the container.

Example A20 includes the system as in example A19, in which the temperature dependent resistive flow sensor produces the electrical signal by detecting a temperature fluctuation when the fluid passes out of the nozzle.

Example A21 includes the system as in example A19, in which the optic flow sensor includes a light emitting diode (LED) positioned at one end of the nozzle and a photodetector positioned at an opposing end of the nozzle operable to receive light emitted by the LED, in which the optic flow sensor produces the electrical signal by detecting, at the photodetector, a change in the refraction index of the emitted light caused when the fluid passes over the nozzle.

Example A22 includes the system as in the example A21, further including an optically emitting element (e.g., such as an LED) in communication with the data processing unit, the optically emitting element operable to emit light at a direction and/or intensity to illuminate the container, in which the data processing unit is configured to control the optically emitting element to emit the light to provide an alert signal indicating to the user that the user should dispense the fluid from the container.

Example A23 includes the system as in example A18, in which the conformal substrate is attached and conformed to the body of the container.

Example A24 includes the system as in example A23, in which the pressure sensor includes a force sensitive resistor (FSR) or a strain gauge, in which the pressure sensor produces the electrical signal corresponding to an amount of pressure change caused by squeezing the body of the container, and in which the processing unit determines if the detected amount of pressure is above or below a threshold value to determine the occurrence of the dispensing event.

Example A25 includes the system as in example A24, in which the position sensor includes a gyroscope or an accelerometer, in which the position sensor produces the electrical signal based on a change in orientation of the container detected by the position sensor.

In another example of the present technology (example A26), a system for monitoring dispensing of a fluid from a container includes a data acquisition unit including a sensor and a signal processing circuit formed in a material structure of a container capable of storing and dispensing a fluid, in which the sensor transduces an occurrence of the fluid dispensing from the container into an electrical signal, and the signal processing circuit amplifies the electrical signal; a data processing unit including a processor and a memory unit, the data processing unit formed in the material structure of the container and in communication with the data acquisition unit to process the amplified electrical signal as data to determine a dispensing event of the fluid from the container; and a communications unit formed in the material structure of the container and in communication with the data processing unit to wirelessly transmit the processed data to a remote device.

Example A27 includes the system as in example A26, in which the data acquisition unit, the data processing unit, and the communications unit are formed in the material structure of the container by a 3D printing process.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination.

Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A device for monitoring patient compliance of a medication, comprising:
    a substrate that is non-frangible, attachable, and conformable to a bottle container containing medicine, wherein the substrate is mechanically flexible and electrically insulative;
    a data acquisition unit including a sensor and a signal processing circuit formed on the substrate, wherein, when the device is attached to the bottle container, the sensor is operable to transduce an occurrence of the medicine being dispensed from the bottle container into an electrical signal, and the signal processing circuit is operable to amplify the electrical signal;
    a data processing unit, including a processor and a memory formed on the substrate and in communication with the data acquisition unit, configured to process the amplified electrical signal as data indicative of the occurrence of a dispensing of the medicine from the bottle container; and
    a communications unit formed on the substrate and in communication with the data processing unit to wirelessly transmit the processed data to a remote device,
    wherein the medicine includes a fluid, and the substrate is attached and conformed to the body of the bottle container,
    wherein the sensor includes a pressure sensor operable to produce the electrical signal corresponding to an amount of pressure change caused by squeezing the body of the bottle container, and wherein the data processing unit is operable to determine whether the amount of pressure change is above or below a threshold value to determine the occurrence of the medicine being dispensed from the bottle container,
    wherein the substrate, the sensor, the signal processing unit, the data processing unit, and the communications unit are configured in a single device package that is attachable and conformable to the bottle container after the medicine has been enclosed or sealed within the bottle container.

2. The device as in claim 1, wherein the device further includes a second sensor includes one or more of a temperature sensor, an optical sensor, or a position sensor.

3. The device as in claim 2, wherein the medicine includes a fluid, and the substrate is attached and conformed at or proximate to a nozzle of the bottle container.

4. The device as in claim 3, wherein the temperature sensor includes a temperature dependent resistive flow sensor operable to produce the electrical signal by detecting a temperature fluctuation when the fluid passes out of the nozzle.

5. The device as in claim 3, wherein the optical sensor includes a light emitting diode (LED) positioned at one end of the nozzle and a photodetector positioned at an opposing end of the nozzle to receive light emitted by the LED, wherein the optical sensor is operable to produce the electrical signal by detecting, at the photodetector, a change in a refraction index of the emitted light caused when the fluid passes out of the nozzle.

6. The device as in claim 1, wherein the pressure sensor includes a force sensitive resistor (FSR) or a strain gauge.

7. The device as in claim 2, wherein the position sensor includes a gyroscope or an accelerometer, wherein the position sensor is operable to produce the electrical signal based on a change in orientation of the bottle container detected by the position sensor.

8. The device as in claim 1, further comprising:
an LED electrically coupled to the signal processing circuit and operable to emit a light when the sensor detects the occurrence of the medicine being dispensed from the bottle container.

9. The device as in claim 1, further comprising:
an alert unit including one or more of an LED, a speaker, or a vibrator in communication with the data processing unit to generate an alert signal from the bottle container.

10. The device as in claim 1, wherein the bottle container includes a droplet bottle or a bottle with a detachable lid, and wherein the device is structured to unobtrusively attach to the bottle container so as to retain the look, feel, and operation of the bottle container.

11. The device as in claim 1, wherein the data processing unit is configured to determine a quantitative amount of the medicine dispensed from the bottle container based on the amplified electrical signal.

12. A method for monitoring dispensing of medicine from a bottle container by a device for monitoring patient compliance of the medicine,
wherein the device that is attached to the bottle container and comprises: (i) a substrate that is non-frangible, attachable, and conformable to the bottle container, the substrate being mechanically flexible and electrically insulative; (ii) a data acquisition unit including a sensor and a signal processing circuit formed on the substrate, wherein the sensor is operable to transduce the medicine being dispensed from the bottle container; (iii) a data processing unit, including a processor and a memory formed on the substrate and in communication with the data acquisition unit; and (iv) a communications unit formed on the substrate and in communication with the data processing unit, wherein the substrate, the sensor, the signal processing unit, the data processing unit, and the communications unit are configured in a single device package that is attachable and conformable to the bottle container after the medicine has been enclosed or sealed within the bottle container, wherein the medicine includes a fluid, and the substrate is attached and conformed to the body of the bottle container, wherein the sensor includes a pressure sensor operable to produce an electrical output corresponding to an amount of pressure change caused by squeezing the body of the bottle container, and wherein the data processing unit is operable to determine whether the amount of pressure change is above or below a threshold value to determine an occurrence of the medicine being dispensed from the bottle container,
the method comprising:
detecting a signal corresponding to the output by the pressure sensor of the device that transduces the occurrence of the medicine dispensing from an opening of the bottle container into an electrical signal, wherein the signal is detected by the sensor without destruction of the bottle container;
amplifying, by the signal processing circuit of the device, the electrical signals; and
processing by the data processing unit, the amplified electrical signal to produce data indicative of the occurrence or a nonoccurrence of the medicine being dispensed from the container.

13. The method as in claim 12, wherein the processing includes associating a time value with a determined occurrence and determining if the time value associated with the determined occurrence is before or after a predetermined time.

14. The method as in claim 12, further comprising:
wirelessly transmitting, by the communications unit of the device to a remote device, the data indicative of the occurrence or the nonoccurrence of the medicine being dispensed from the bottle container.

15. The method as in claim 14, further comprising:
producing an alert corresponding to a message indicating a predetermined dispensing event for a user to take the medicine is upcoming, the predetermined dispensing event has occurred, or the predetermined dispensing event has been missed.

16. The method as in claim 12, further comprising:
determining compliance of a user using the medicine according to a particular schedule of use for the user; and
generating a message indicating the dispensing event was early or late based on the predetermined time.

17. A device for monitoring dispensing of a fluid from a container, comprising:
a data acquisition unit including a sensor and a signal processing circuit formed in a non-frangible, attachable, and conformal substrate attachable to a material structure of a bottle container capable of storing and dispensing a fluid, wherein the sensor transduces an occurrence of the fluid dispensing from the bottle container into an electrical signal, and the signal processing circuit amplifies the electrical signal;
a data processing unit including a processor and a memory unit, the data processing unit formed in the substrate attachable to the material structure of the bottle container and in communication with the data acquisition unit to process the amplified electrical signal as data to determine a dispensing event of the fluid from the bottle container; and
a communications unit formed in the substrate attachable to the material structure of the bottle container and in communication with the data processing unit to wirelessly transmit the processed data to a remote device,
wherein the substrate is attached and conformed to the body of the bottle container,
wherein the sensor includes a pressure sensor operable to produce the electrical signal corresponding to an amount of pressure change caused by squeezing the body of the bottle container, and wherein the data processing unit is operable to determine whether the amount of pressure change is above or below a threshold value to determine the occurrence of the fluid being dispensed from the bottle container, wherein the substrate, the sensor, the signal processing unit, the data processing unit, and the communications unit are configured in a single device package that is attachable and conformable to the bottle container after the medicine has been enclosed or sealed within the bottle container.

18. The device as in claim 17, wherein the bottle container includes a droplet bottle or a bottle with a detachable lid.

19. The device as in claim 17, wherein the device further includes a second sensor includes one or more of a temperature sensor, an optical sensor, or a position sensor.

20. The device as in claim 17, wherein the sensor is configured at or proximate to a nozzle of the bottle container in the substrate.

21. The device as in claim 17, wherein the pressure sensor includes a force sensitive resistor (FSR) or a strain gauge.

22. The device as in claim 19, wherein the position sensor includes a gyroscope or an accelerometer, wherein the position sensor is operable to produce the electrical signal based on a change in orientation of the bottle container detected by the position sensor.

* * * * *